(12) United States Patent
Martinez Arranz et al.

(10) Patent No.: US 11,899,027 B2
(45) Date of Patent: Feb. 13, 2024

(54) DIAGNOSTIC METHODS BASED ON LIPID PROFILES

(71) Applicant: RUBIO METABOLOMICS, S.L.U., Derio-Bizkaia (ES)

(72) Inventors: Ibon Martinez Arranz, Derio-Bizkaia (ES); Rebeca Mayo Sanchez, Derio-Bizkaia (ES); Azucena Castro Espido, Derio-Bizkaia (ES); Jose Maria Mato De La Paz, Bizkaia (ES)

(73) Assignee: RUBIO METABOLOMICS, S.L.U., Derio-Bizkaia (ES)

( * ) Notice: Subject to any disclaimer, the term of this patent is extended or adjusted under 35 U.S.C. 154(b) by 139 days.

(21) Appl. No.: 16/313,021

(22) PCT Filed: Jul. 6, 2017

(86) PCT No.: PCT/EP2017/066915
§ 371 (c)(1),
(2) Date: Dec. 22, 2018

(87) PCT Pub. No.: WO2018/007511
PCT Pub. Date: Jan. 11, 2018

(65) Prior Publication Data
US 2019/0219602 A1    Jul. 18, 2019

(30) Foreign Application Priority Data
Jul. 6, 2016 (EP) .................................... 16382320

(51) Int. Cl.
*G01N 33/92* (2006.01)

(52) U.S. Cl.
CPC ......... *G01N 33/92* (2013.01); *G01N 2405/02* (2013.01); *G01N 2560/00* (2013.01); *G01N 2570/00* (2013.01); *G01N 2800/085* (2013.01)

(58) Field of Classification Search
CPC ........................................................ G01N 33/92
See application file for complete search history.

(56) References Cited

U.S. PATENT DOCUMENTS

| 4,540,884 A | 9/1985 | Stafford et al. |
| 5,397,894 A | 3/1995 | Wells et al. |

(Continued)

FOREIGN PATENT DOCUMENTS

| WO | WO2008021192 A2 | 2/2008 |
| WO | WO2011140093 A2 | 11/2011 |

(Continued)

OTHER PUBLICATIONS

Prediction of non-alcoholic fatty liver disease and liver fat content by serum molecular lipids. Oresic et al. Diabetologia (2013) 56:2266-2274 (Year: 2013).*

(Continued)

*Primary Examiner* — Brian R Gordon
*Assistant Examiner* — Dwan A Gerido
(74) *Attorney, Agent, or Firm* — Hultquist, PLLC; Steven J. Hultquist

(57) ABSTRACT

The present invention relates to methods for the diagnosis of NAFLD in a subject, and for the differential diagnosis of NASH or steatosis in a subject suffering from NAFLD, based on the determination in a sample of metabolic markers, particularly lipid metabolic markers.

7 Claims, 20 Drawing Sheets

(56) References Cited

U.S. PATENT DOCUMENTS

| | | | |
|---|---|---|---|
| 2006/0173629 A1 | 8/2006 | Poynard | |
| 2013/0056630 A1* | 3/2013 | Feldstein | G16H 50/30 250/282 |
| 2017/0370954 A1* | 12/2017 | Perichon | G01N 33/50 |

FOREIGN PATENT DOCUMENTS

| | | |
|---|---|---|
| WO | WO2012000770 A1 | 1/2012 |
| WO | WO2012143514 A1 | 10/2012 |
| WO | WO2013113992 A1 | 8/2013 |
| WO | WO2016081534 A1 | 5/2016 |

OTHER PUBLICATIONS

Fahy, E., et al., "Update of the Lipid Maps comprehensive classification system for lipids", "Journal of Lipid Research", Dec. 19, 2008, pp. S9-S14, vol. 50, Publisher: JLR Papers in Press.

Martinez-Arranz, I., et al., "Enhancing Metabolomics Research Through Data Mining", "Journal of Proteomics", 2015, pp. 1-39.

Niessen, W, et al., "Liquid chromatography-mass spectrometry General principles and instrumentation", "Journal of Chromatography", 1995, pp. 37-57, vol. 703, Publisher: Elsevier Science B.V.

Oresic, M., et al., "Prediction of Non-Alcoholic Fatty-Liver Disease and Liver Fat Content by Serum Molecular Lipids", "Diabetologia", 2013, pp. 2266-2274, vol. 56.

Siegert, S., et al., "Diagnosing Fatty Liver Disease: A Comparative Evaluation of Metabolic Markers, Phenotypes, Genotypes and Established Biomarkers", "PLOS One", 2013, p. e76813: 1-12, vol. 8, No. 10.

\* cited by examiner

TG(44:1)

TG(46:0)

TG(16:0+16:0+14:0)

TG(48:0)

TG(16:0/16:0/16:0)

TG(48:1)

TG(49:1)

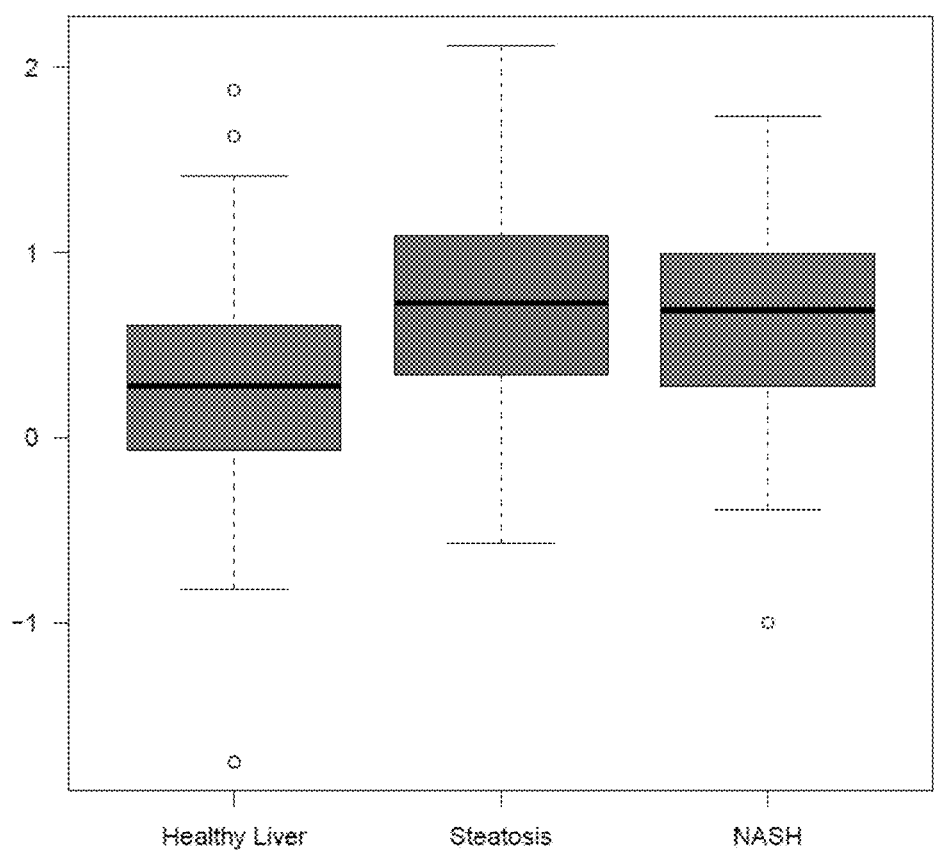
Fig. 1F TG(50:2)

TG(52:1)

TG(53:0)

TG(53:1)

TG(54:5)

TG(58:2)

TG(44:1)

TG(14:0+18:1+12:0) + TG(16:0+16:1+12:0)

TG(48:2)

TG(14:0+18:1+16:1) + TG(16:0+18:2+14:0)

TG(49:1)

TG(50:1)

TG(50:2)

TG(16:0+18:1+16:1) + TG(18:1+18:1+14:0) + TG(16:0+18:2+16:0)

TG(51:1)

TG(16:0+17:0+18:1)

TG(51:2)

TG(16:0+17:1+18:1)

TG(51:3)

TG(16:0+17:1+18:2) + TG(18:2+18:1+15:0)

TG(52:0)

TG(52:2)

TG(52:3)

TG(52:4)

TG(53:3)

TG(54:2)

TG(54:3)

TG(20:2+20:1+14:0) + TG(20:2+18:1+16:0) + TG(20:1+18:2+16:0) + TG(18:2+18:1+18:0)

TG(54:5)

TG(18:1+20:4+16:0)

TG(54:6)

TG(56:3)

TG(56:7)

TG(56:8)

US 11,899,027 B2

DIAGNOSTIC METHODS BASED ON LIPID PROFILES

CROSS-REFERENCE TO RELATED APPLICATIONS

This application is a U.S. national phase under the provisions of 35 U.S.C. § 371 of International Patent Application No. PCT/EP17/66915 filed Jul. 6, 2017, which in turn claims priority under 35 U.S.C. § 119 of European Patent Application No. 16382320.6 filed Jul. 6, 2016. The disclosures of such international patent application and European priority patent application are hereby incorporated herein by reference in their respective entireties, for all purposes.

TECHNICAL FIELD

The present invention relates to methods for non-invasive diagnosis of non-alcoholic fatty liver disease (NAFLD). The invention further relates to diagnostic methods for non-alcoholic steatohepatitis (NASH) vs. fatty liver (steatosis). These methods rely on the determination of lipid metabolic markers in a biological sample of the patient, wherein their expression is up- or down-regulated in the NAFLD patients vs. healthy patients, and NASH patients vs. steatosis patients.

BACKGROUND ART

Non-alcoholic fatty liver disease (NAFLD) encompasses a wide range of conditions characterized by the build-up of fat in the liver cells in absence of alcohol abuse. At one end of the scale is the relatively harmless simple fatty liver, or steatosis, that does not cause significant liver damage. If left unattended, this condition may progress to more advanced conditions, some of which may be life threatening. Non-alcoholic steatohepatitis (NASH) is a significant development in NAFLD, corresponding to an aggressive condition characterized by swelling and tenderness in the liver. With intense, on-going inflammation a buildup of scar tissue (fibrosis) may form, eventually leading to cirrhosis where irregular bumps, known as nodules, replace the smooth liver tissue and the liver becomes harder. The effect of this, together with continued scarring from fibrosis, means that the liver will run out of healthy cells to support normal functions. This can lead to complete liver failure.

NAFLD is the most common cause of chronic liver disease worldwide. It is considered a direct consequence of the rising global epidemic of obesity and the associated increase in the prevalence of diabetes. Most people with a fatty liver are overweight or obese. As more and more people lead inactive lives and carry extra weight around with them, so the number of cases of fatty liver, in particular NASH is rising.

There is currently no specific laboratory test for NASH, making it extremely difficult to diagnose since it is a silent disease and even people who go on to develop fibrosis and cirrhosis may undergo liver damage for many years before symptoms become apparent.

NAFLD may be suspected in subjects with one or more components of the metabolic syndrome, especially obesity and type 2 diabetes and elevated serum aminotransferase levels [alanine aminotransferase (ALT) and aspartate aminotransferase (AST)] in the absence of alcohol abuse or other common causes of liver disease. The only widely accepted test for distinguishing NASH from other forms of disease is a liver biopsy. This process involves passing a fine hollow needle through the skin and into the liver, withdrawing a small tissue of sample that is submitted for histological examination. Apart from the obvious discomfort induced by this invasive procedure, assessment is often subjective and prone to sampling error.

WO08021192 describes a non-invasive method for the diagnosis and monitoring of liver diseases such as NASH and steatosis based on the determination of levels of fatty acids and eicosanoids in a body fluid of the patient. However, this method is limited to the identification of lipid species and requires complex fractionation steps of the body fluids before the metabolites can be detected.

WO12143514 relates to a method for the diagnosis of liver damage, among this liver damage is comprised NAFLD, in a subject comprising determining in a biological sample of said subject the levels of a panel of metabolic markers. However the method has been performed considering the metabolites detected in rat serum extracts and comparing their levels with the degree of apoptosis present in the liver cells. Liver damage therefore can be of any nature.

WO2013113992 describes a method to determine the amount of liver fat and diagnosing NAFLD based in the determination of certain molecular lipids in a blood sample, however, this document does not distinguish between NASH/steatosis within NAFLD patients.

Clearly there is a need for accurate, non-invasive methods to diagnose NAFLD and NASH, in order to better understand where is the patient located within the spectrum of phenotypes that can progress to cirrhosis.

BRIEF SUMMARY OF THE INVENTION

The authors of the present invention have identified a series of lipid metabolic markers present in the serum samples (collected at the time of liver biopsy) comprising samples from control subjects in the absence of NAFLD, and subjects classified with NAFLD. These metabolic markers can then be used in a rapid non-invasive diagnostic method for diagnosing NAFLD.

It is further identified a different lipid metabolic profile to distinguish between NASH and steatosis to be applied optionally on the NAFLD positive patients.

Thus, in a first aspect, the present invention is related to an in vitro method for the diagnosis of non-alcoholic fatty liver disease (NAFLD) in a subject that comprises
 (i) Determining the levels of one or more metabolic markers according to Table 1 in a sample from the subject, and
 (ii) Comparing the levels obtained in (i) to a reference value, wherein the subject is diagnosed with NAFLD according to a score that is obtained by introducing the values of said metabolic marker(s) in a logistic regression model.

In a further aspect, the invention relates to an in vitro method for the diagnosis of non-alcoholic steatohepatitis (NASH) or steatosis in a subject suffering from NAFLD that comprises
 (i) Determining the levels of one or more metabolic markers according to Table 3 in a sample from the subject, and
 (ii) Comparing the levels obtained in (i) to a reference value, wherein the subject is diagnosed of NASH or of steatosis according to a predictive factor or score that is obtained when introducing the values of said metabolic marker(s) in a logistic regression model.

DETAILED DESCRIPTION OF THE INVENTION

Figure 1A:
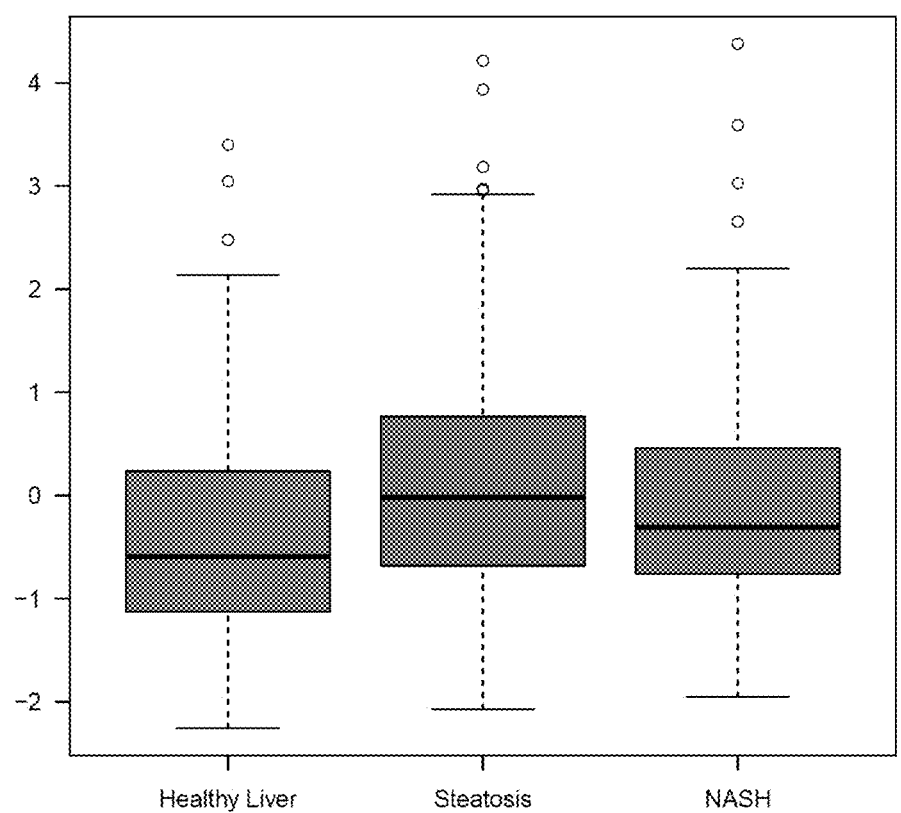
FIG. 1. Box-plot graphs showing levels of metabolic markers according to Table 1 as determined in serum samples from healthy (first), steatosis (second) and NASH (third) patients. A. TG(44:1). B. TG(46:0). C. TG(48:0). D. TG(48:1). E. TG(49:1). F. TG(50:2). G. TG(52:1). H. TG(53:0). I. TG(53:1). J. TG(54:5). K. TG(58:2).
Figure 1B:
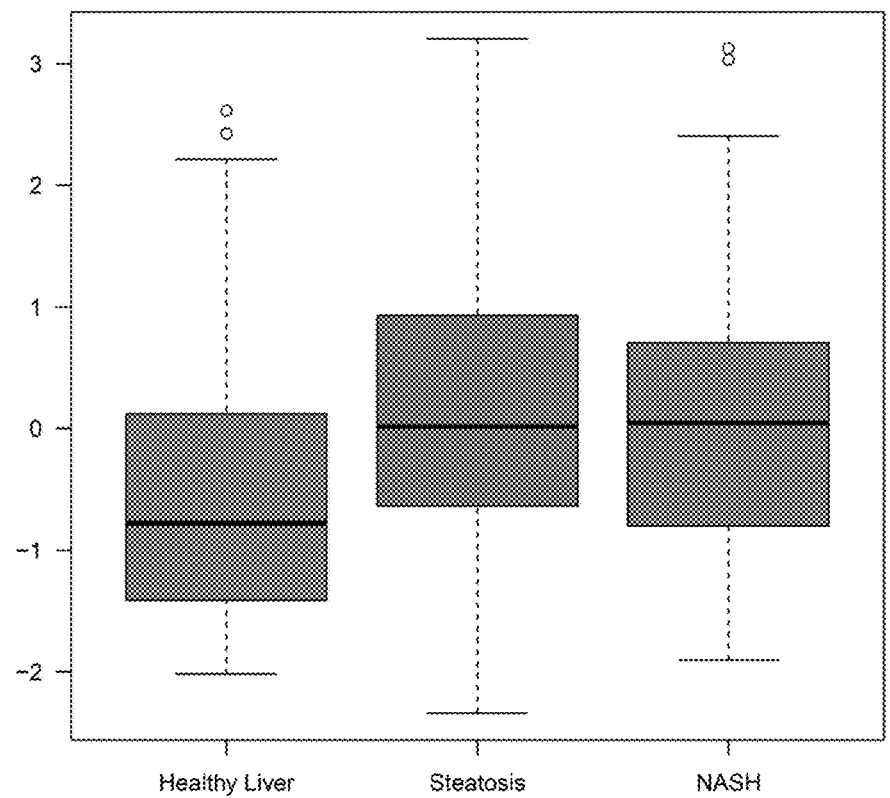
Figure 1C:
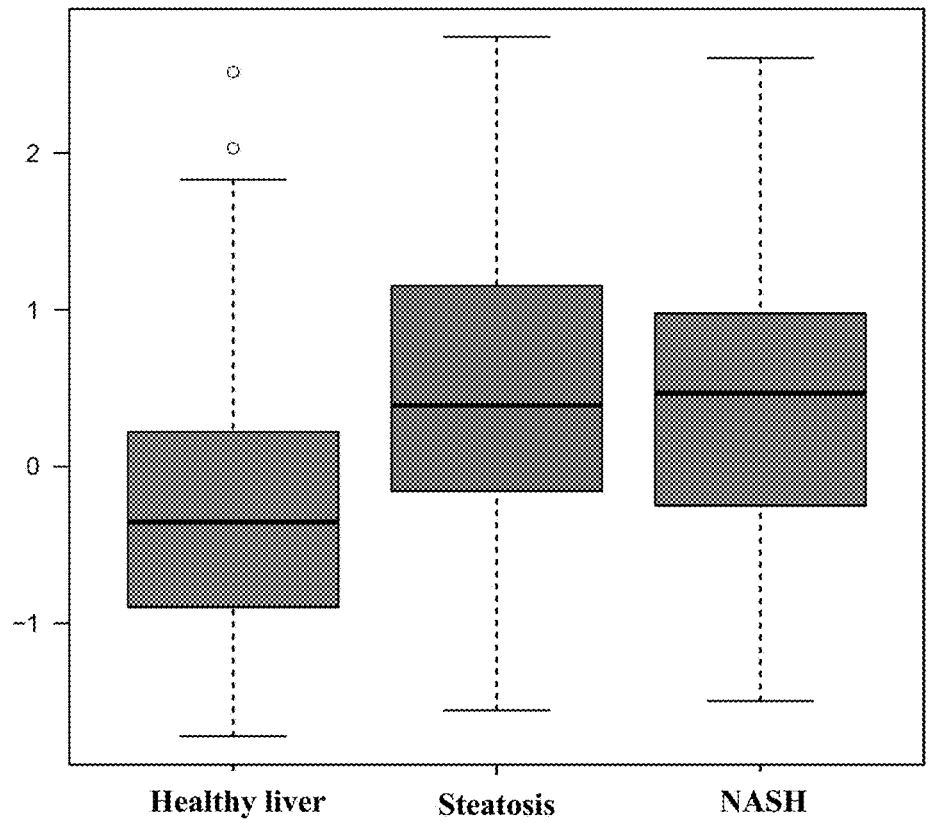
Figure 1D:
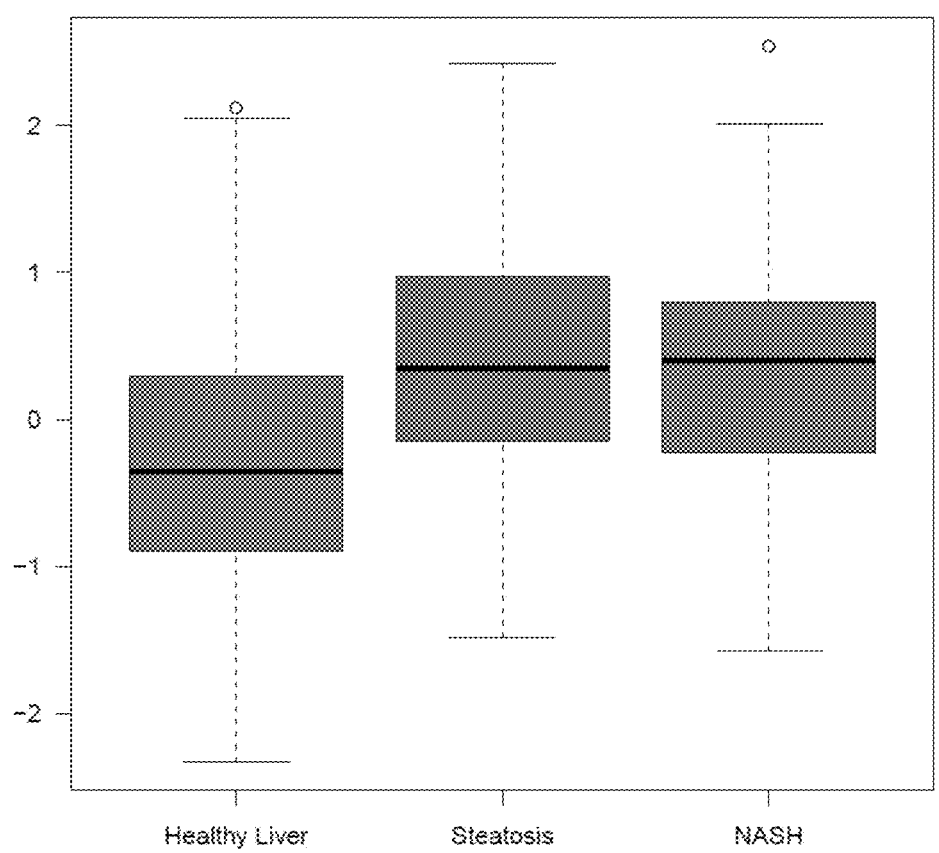
Figure 1E:
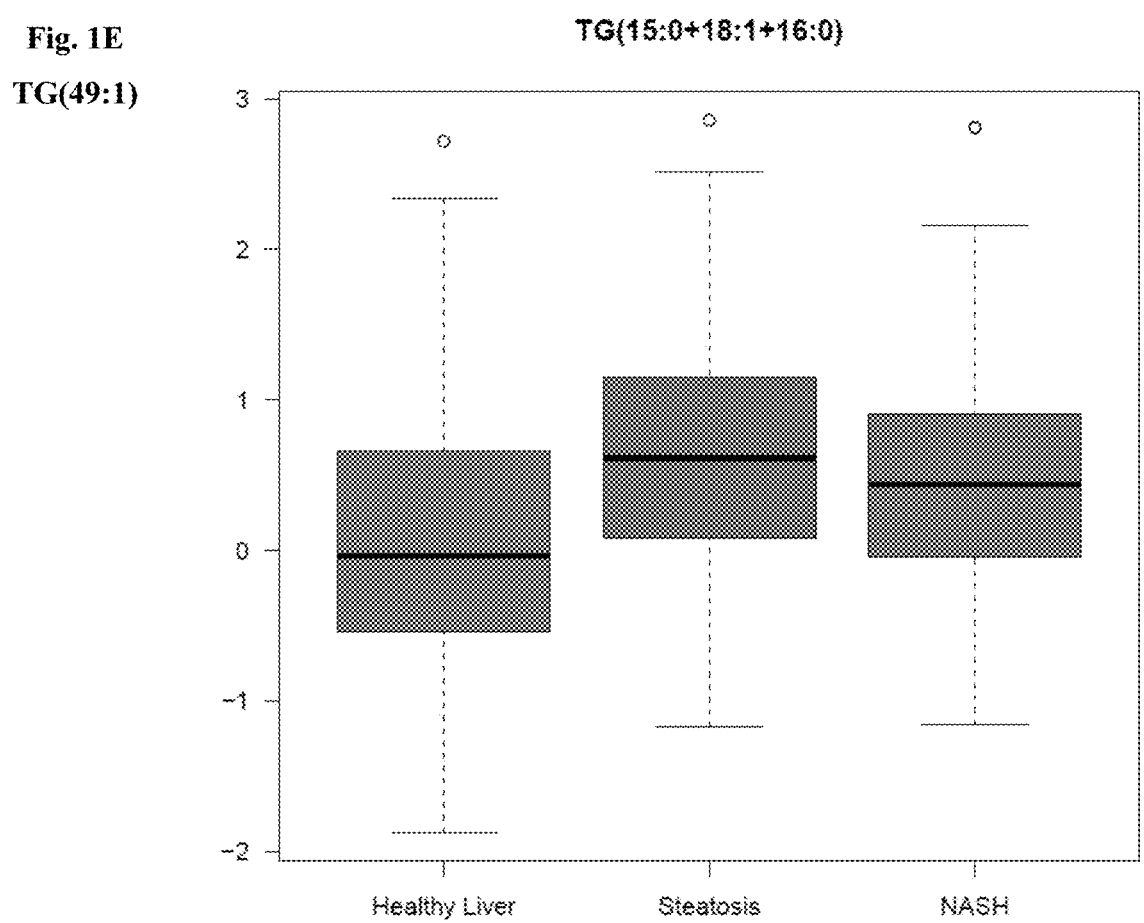
Figure 1G:
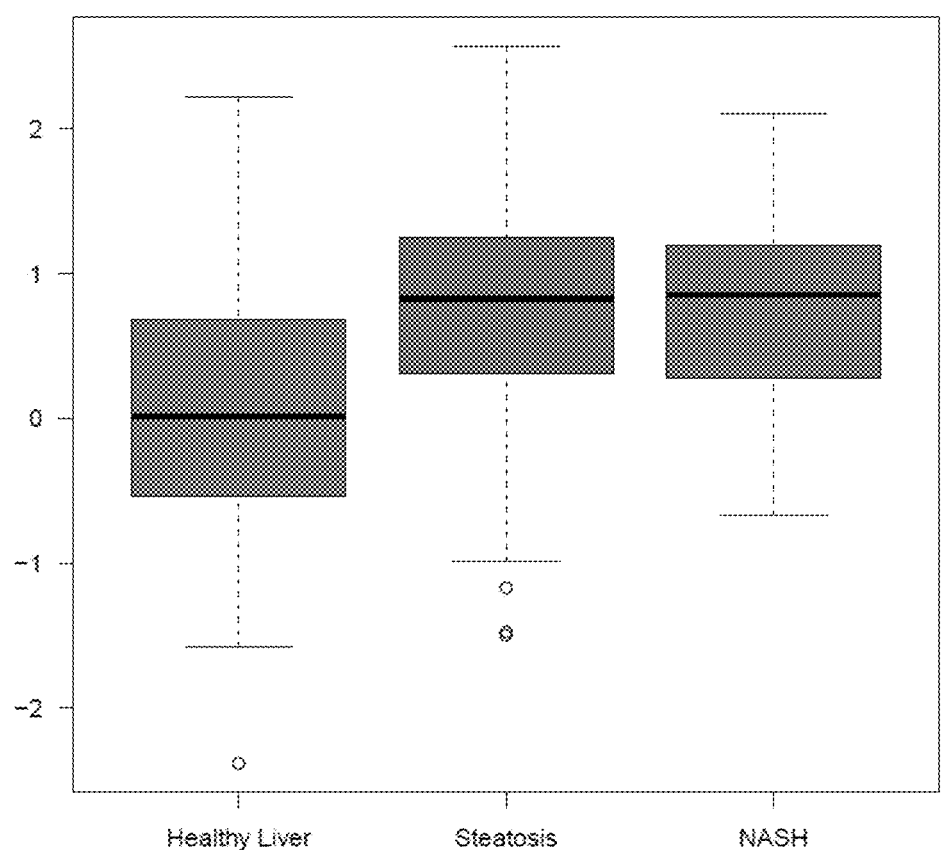
Figure 1H:
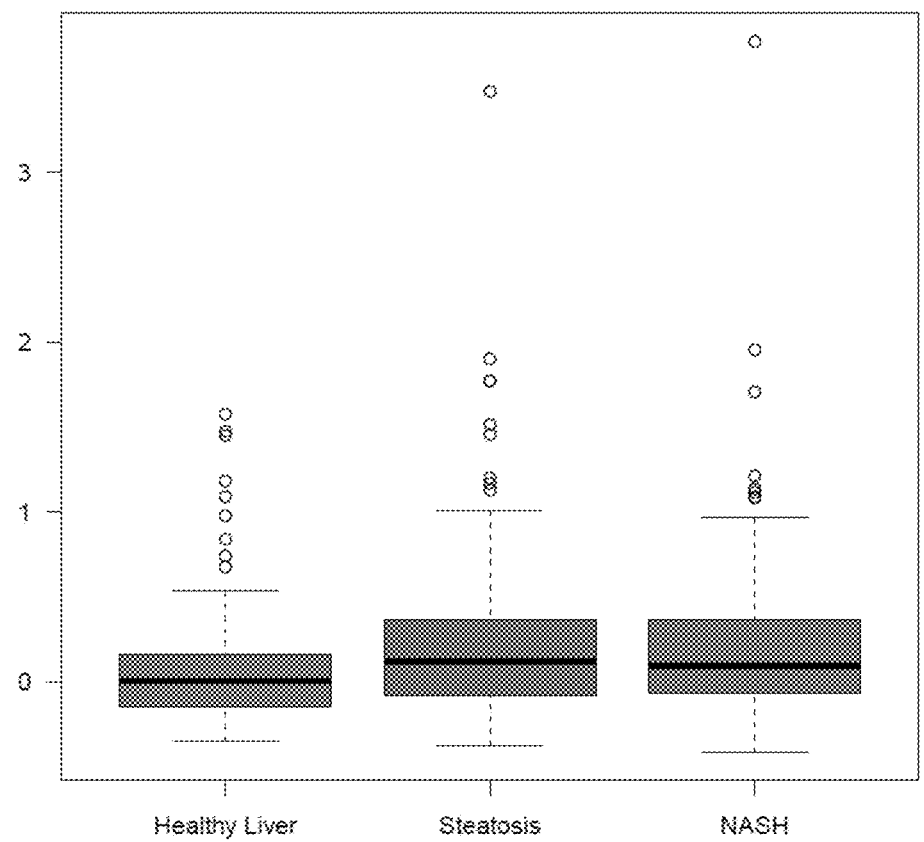
Figure 1I:
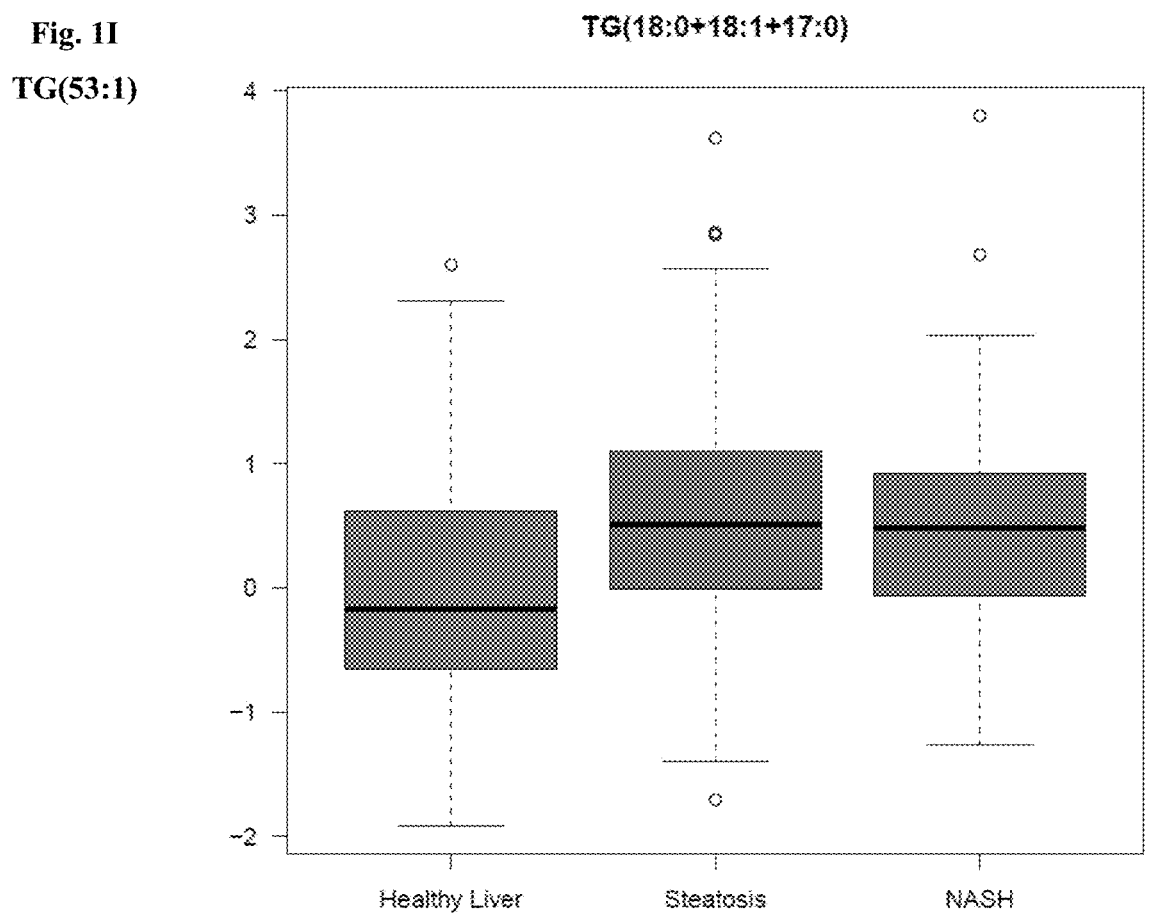
Figure 1J:
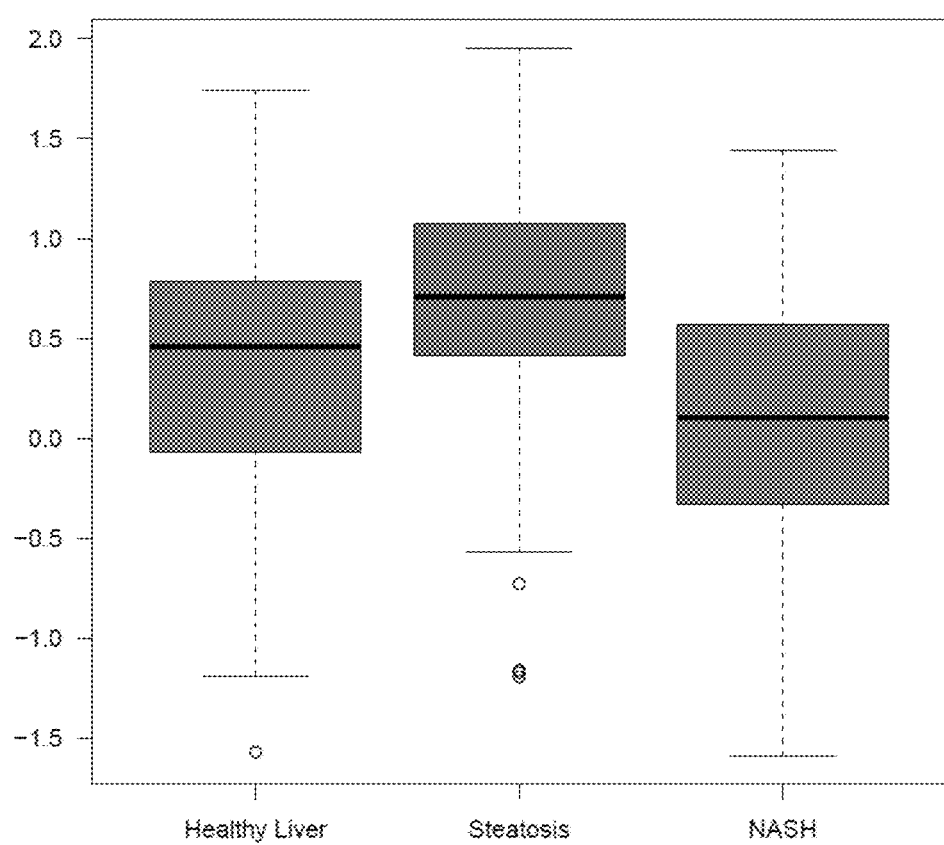
Figure 1K:
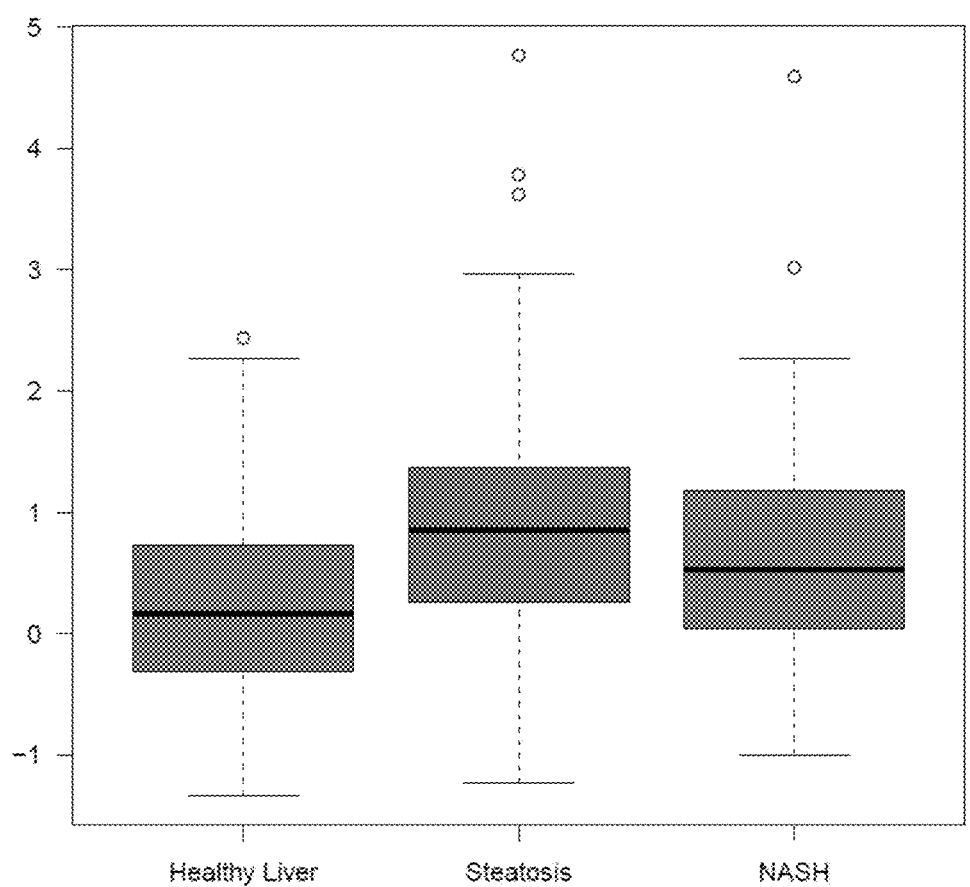
Figure 2A:
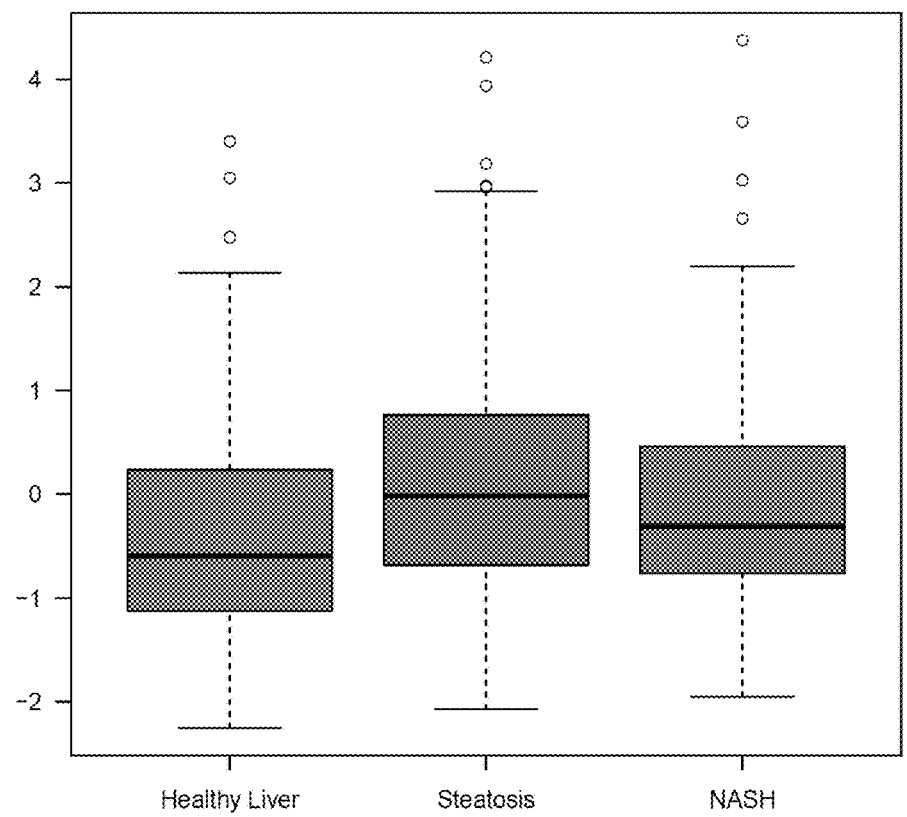
FIG. 2. Box-plot graphs showing levels of metabolic markers according to Table 3 as determined in serum samples from healthy (first), steatosis (second) and NASH (third) patients. A. TG(44:1). B. TG(48:2). C. TG(49:1). D. TG(50:1). E. TG(50:2). F TG(51:1). G. TG(51:2). H. TG(51:3). I. TG(52:0). J. TG(52:2). K. TG(52:3). L. TG(52:4). M. TG(53:3). N. TG(54:2). O. TG(54:3). P. TG(54:5). Q. TG(54:6). R. TG(56:3). S. TG(56:7). T. TG(56:8).
Figure 2B:
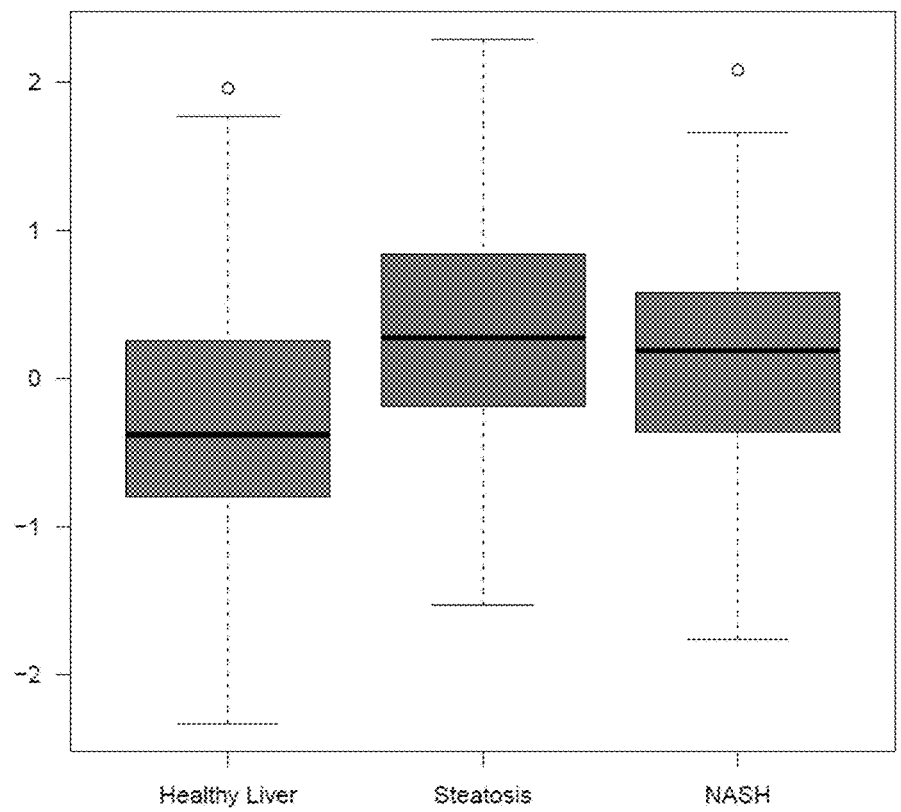
Figure 2C:
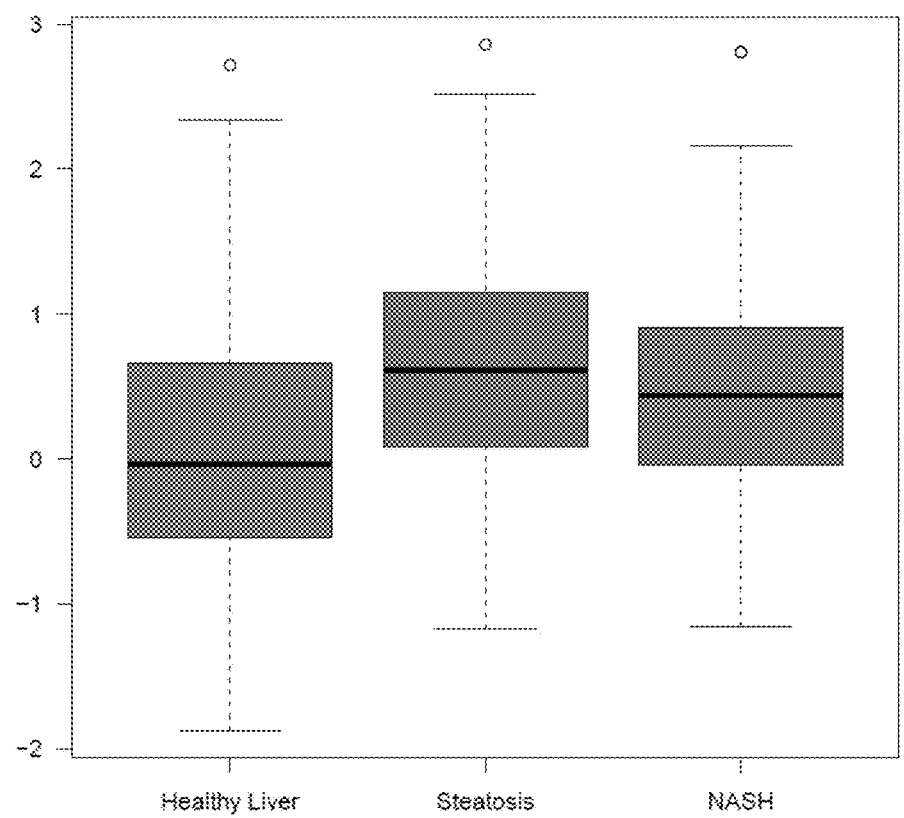
Figure 2D:
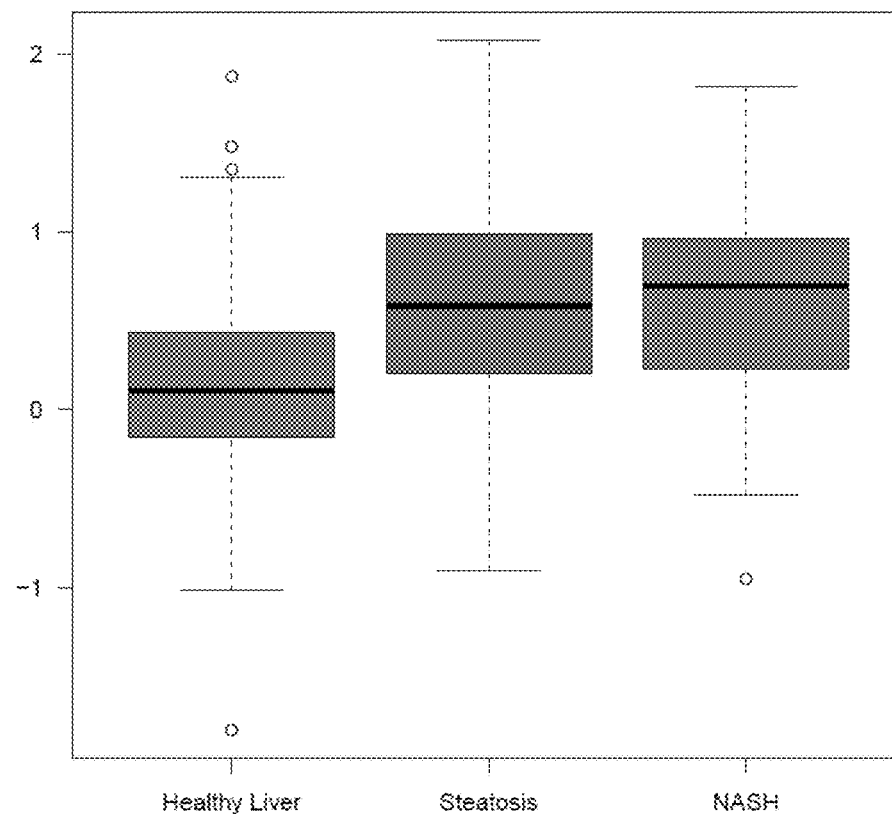
Figure 2E:
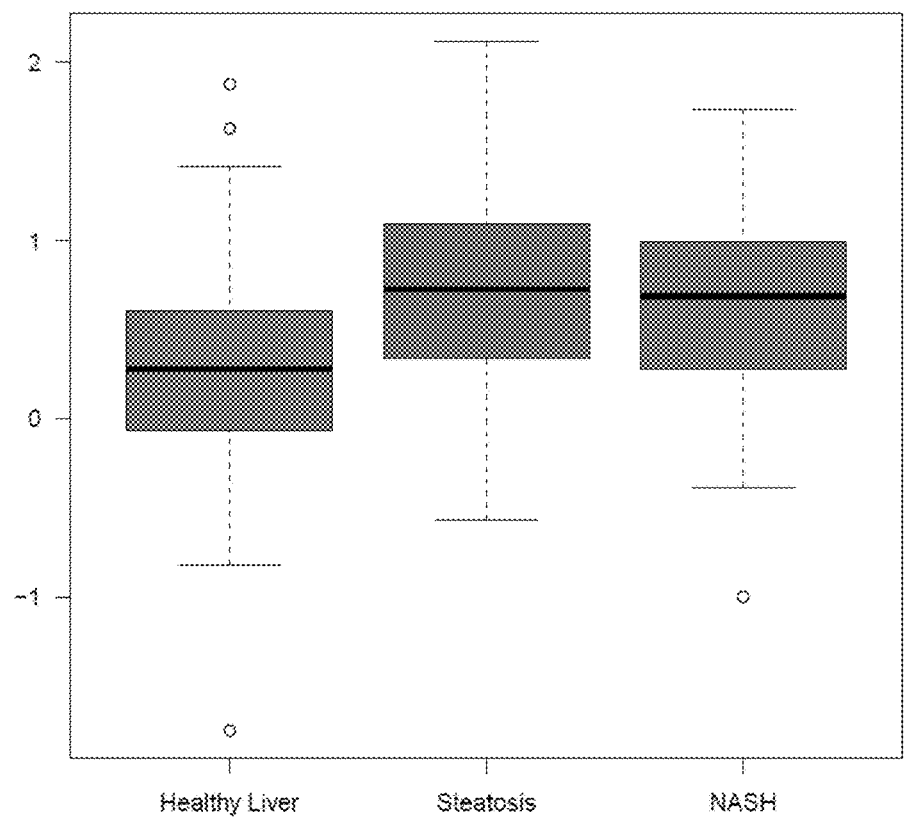
Figure 2F:
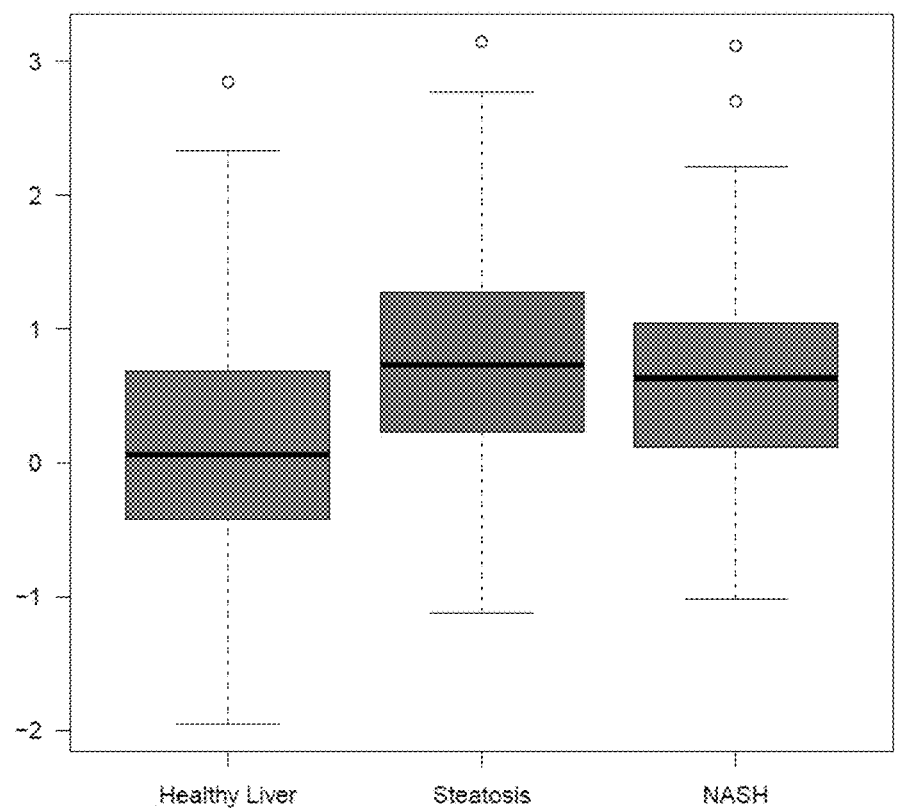
Figure 2G:
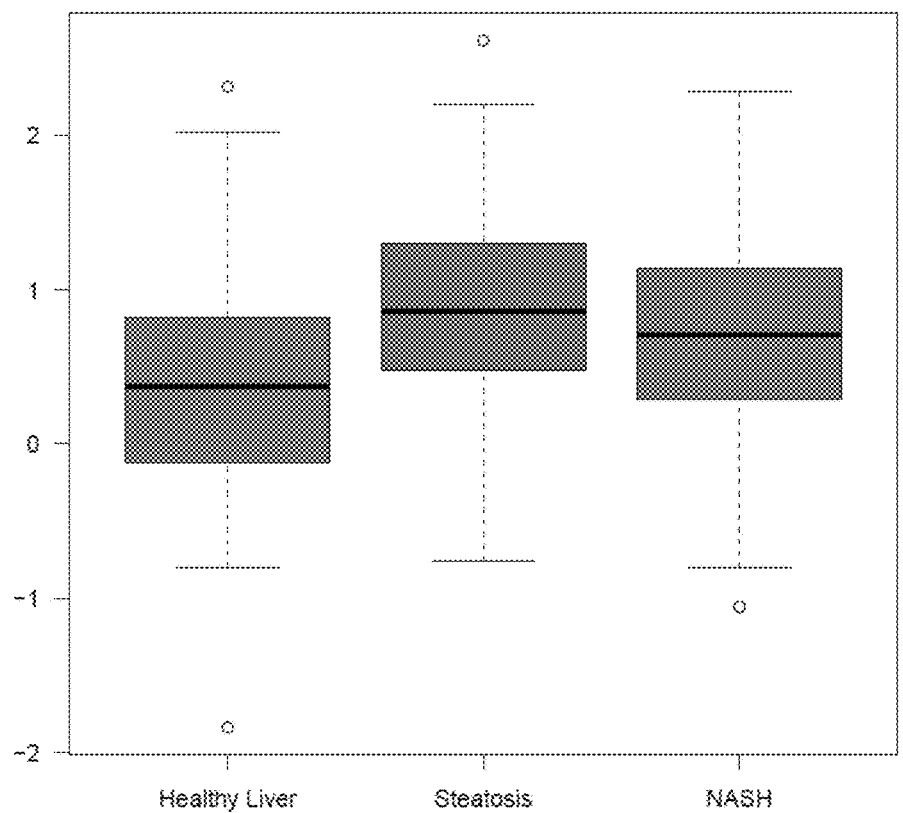
Figure 2H:
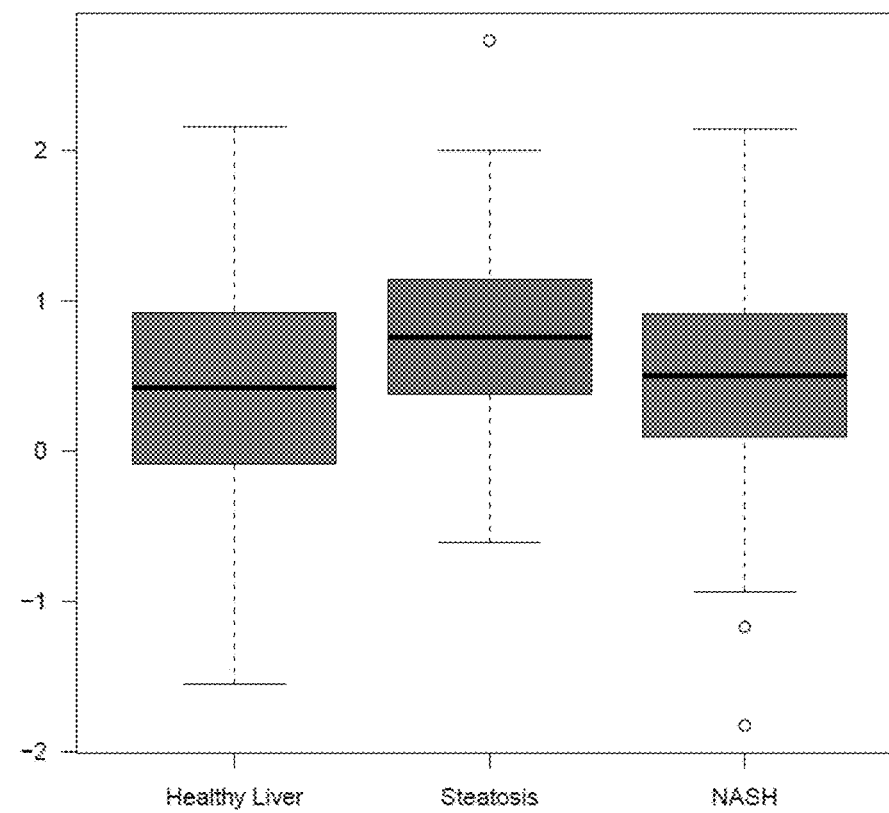
Figure 2I:
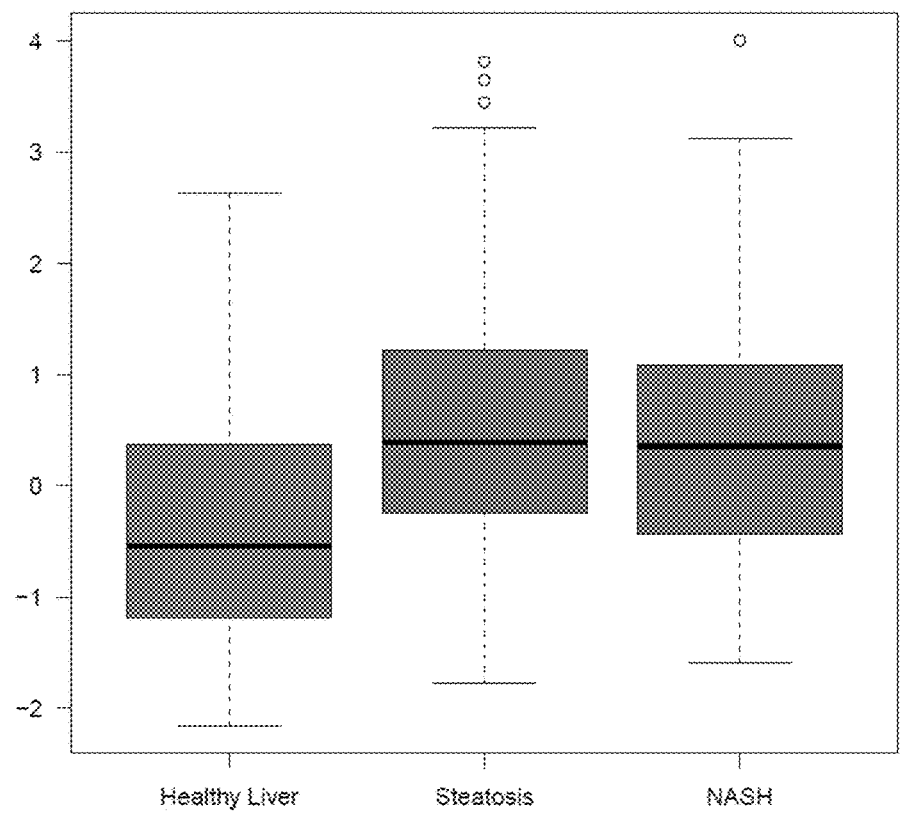
Figure 2J:
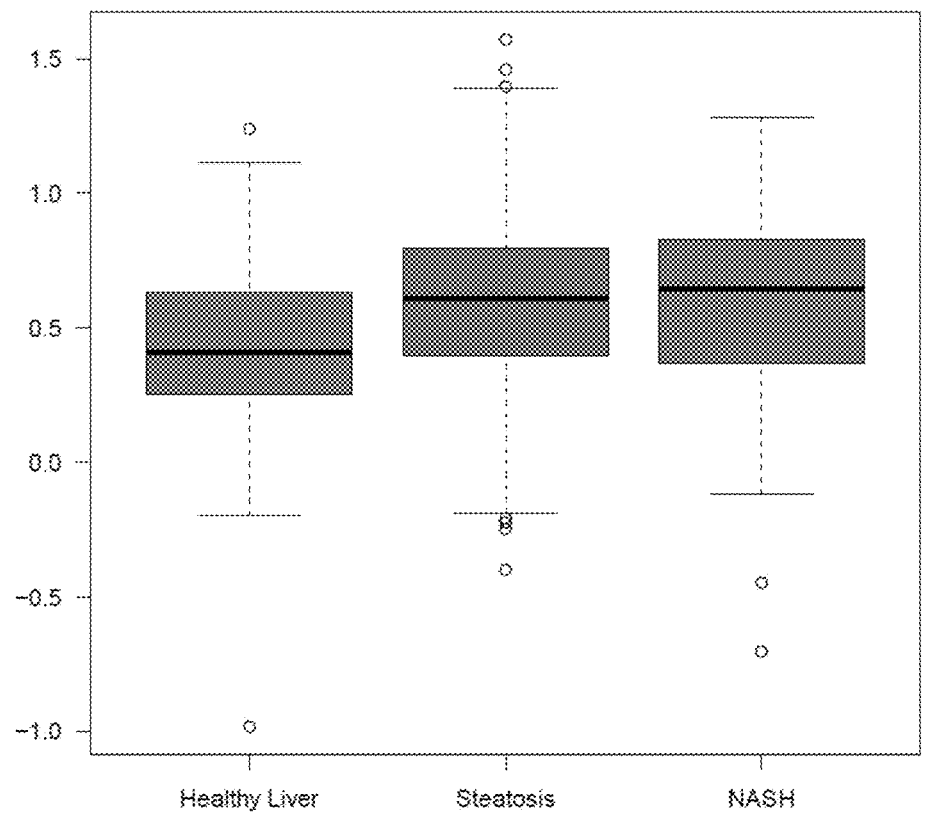
Figure 2K:
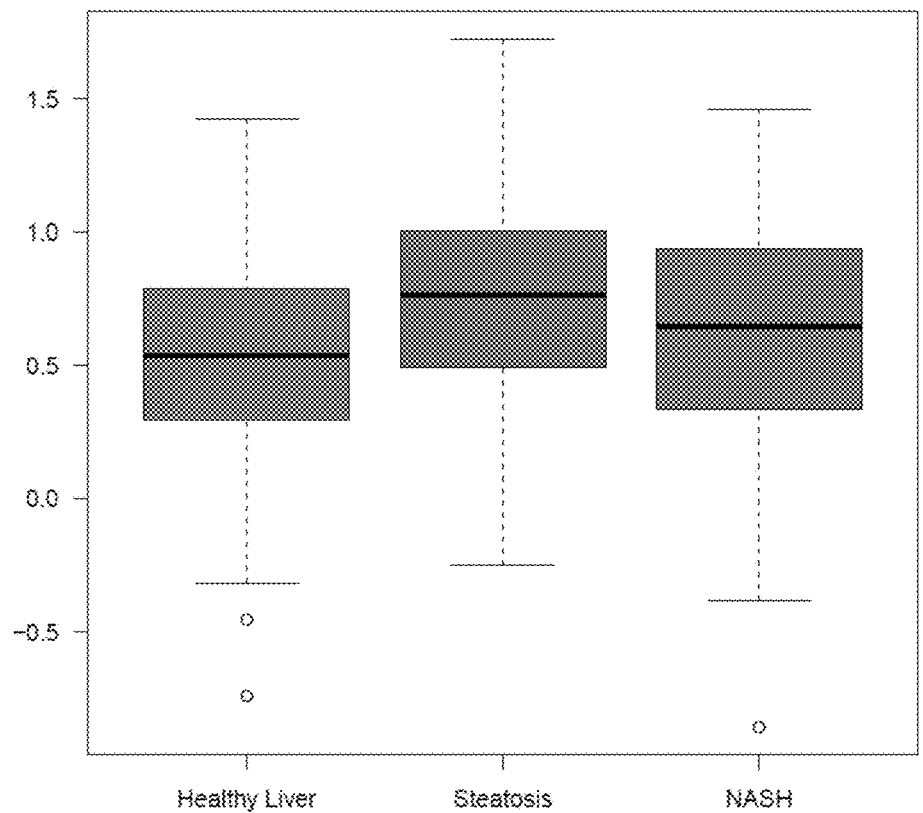
Figure 2L:
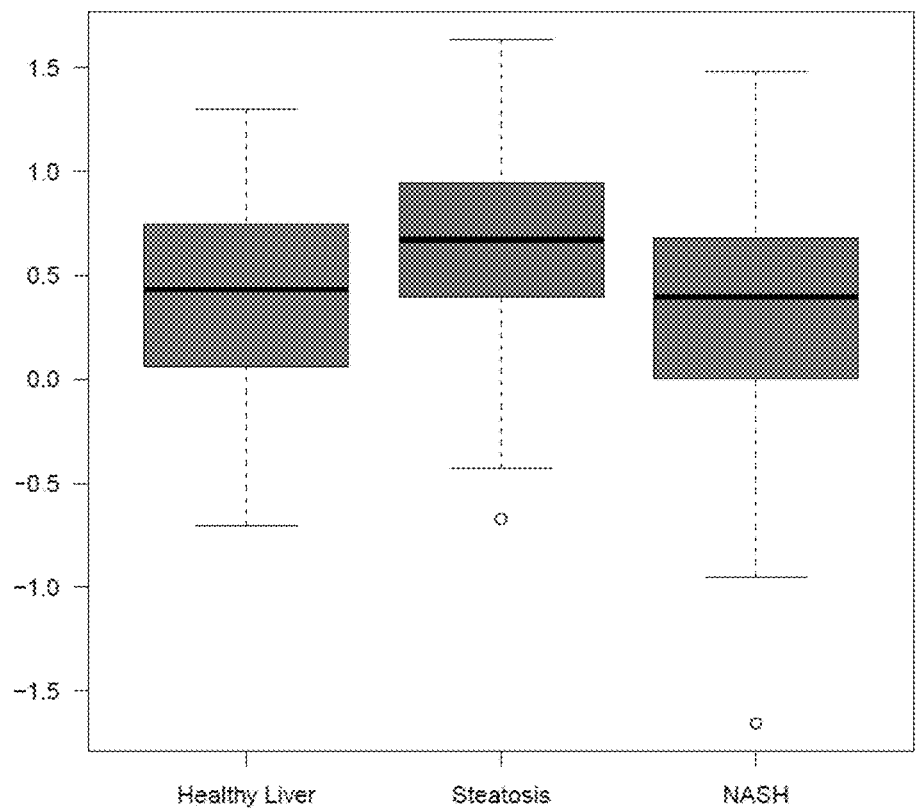
Figure 2M:
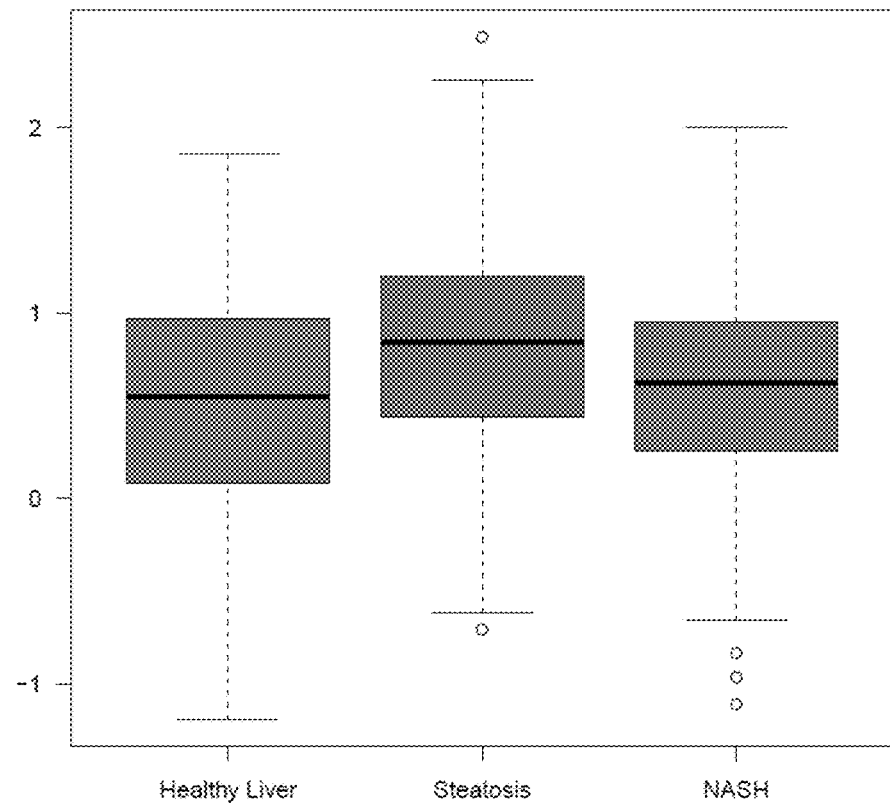
Figure 2N:
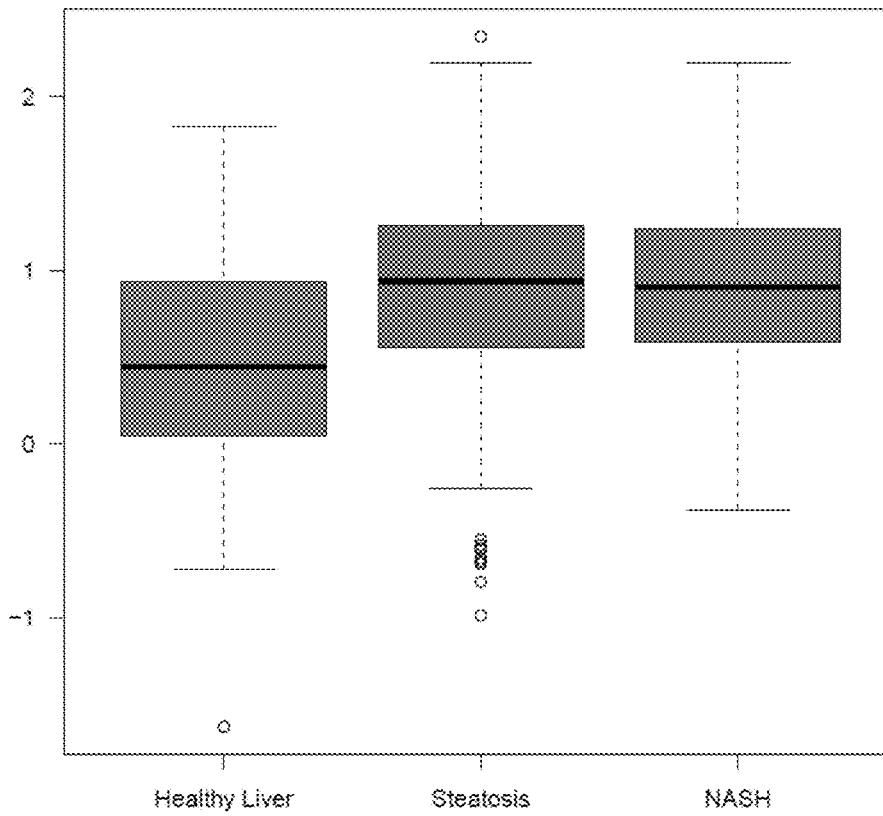
Figure 2O:
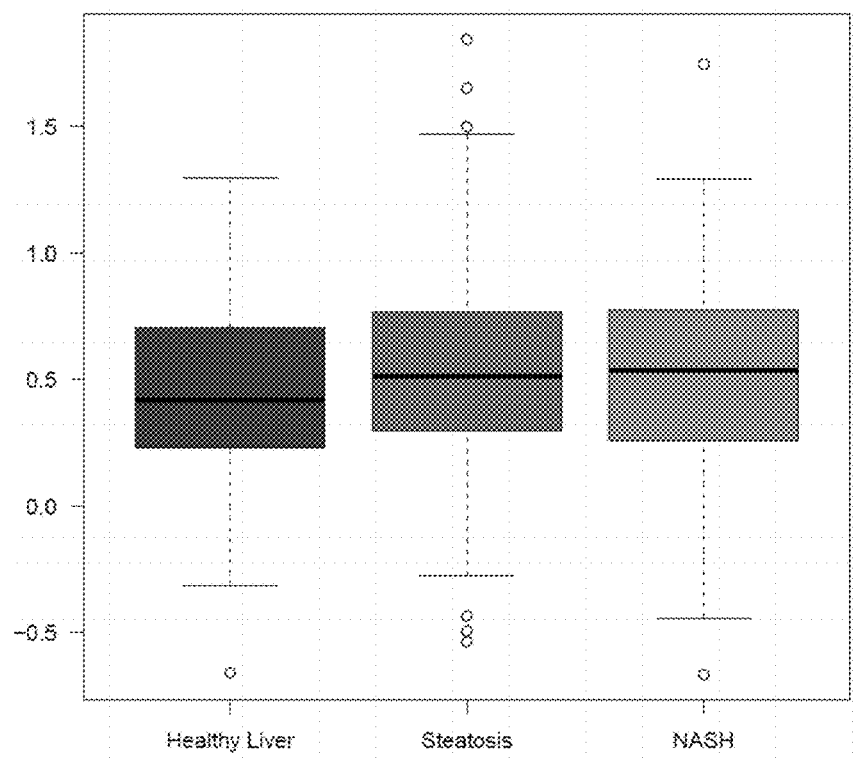
Figure 2P:
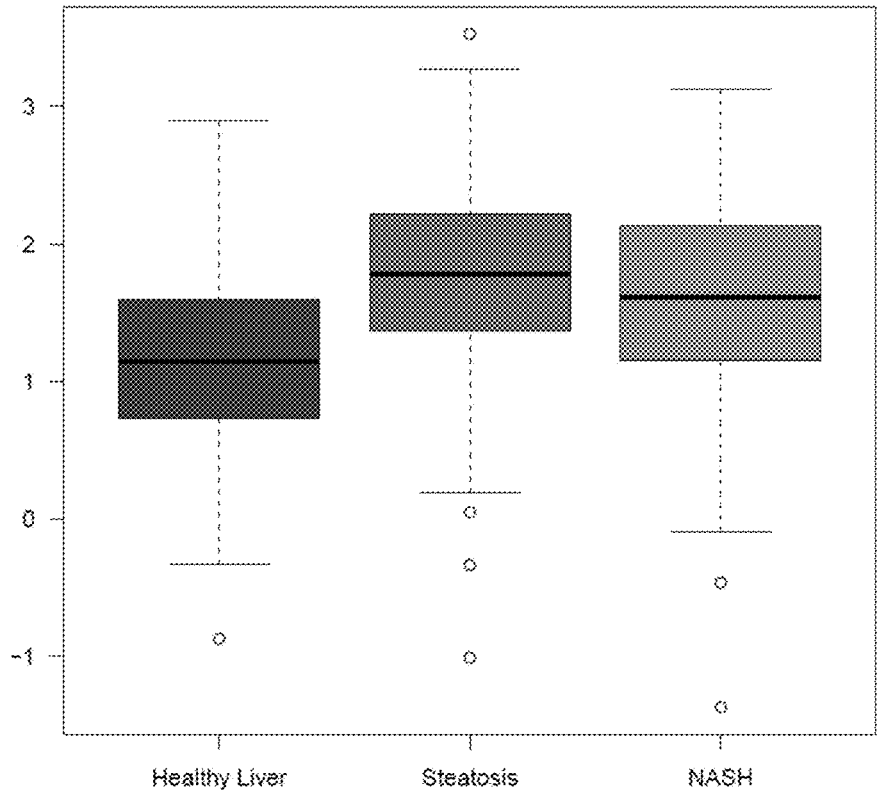
Figure 2Q:
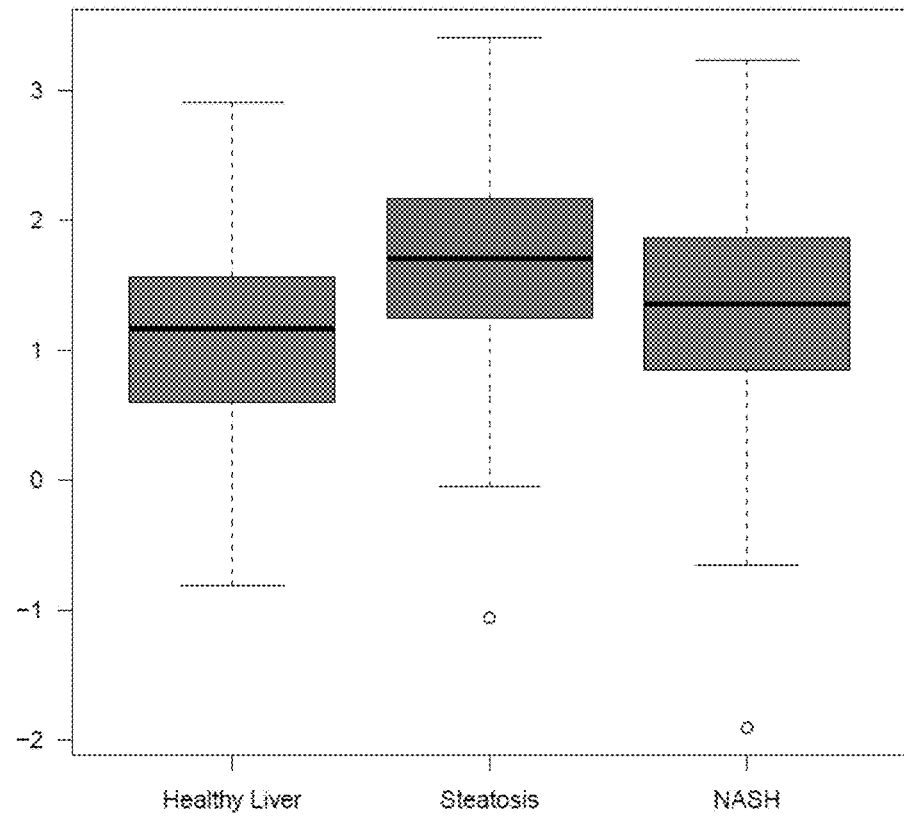
Figure 2R:
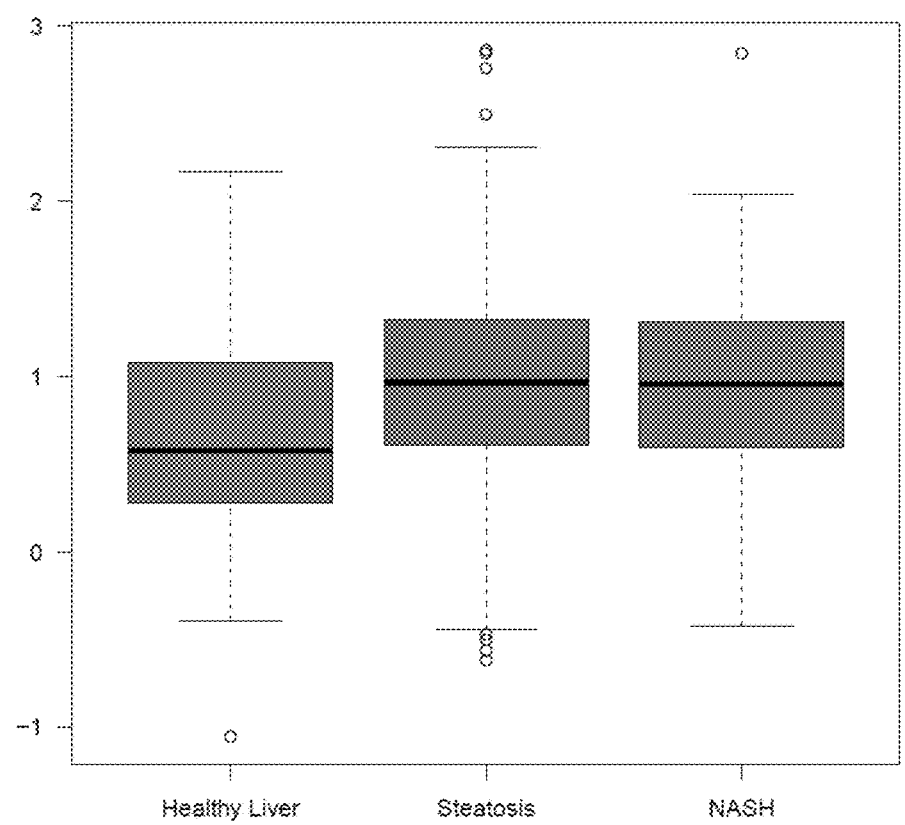
Figure 2S:
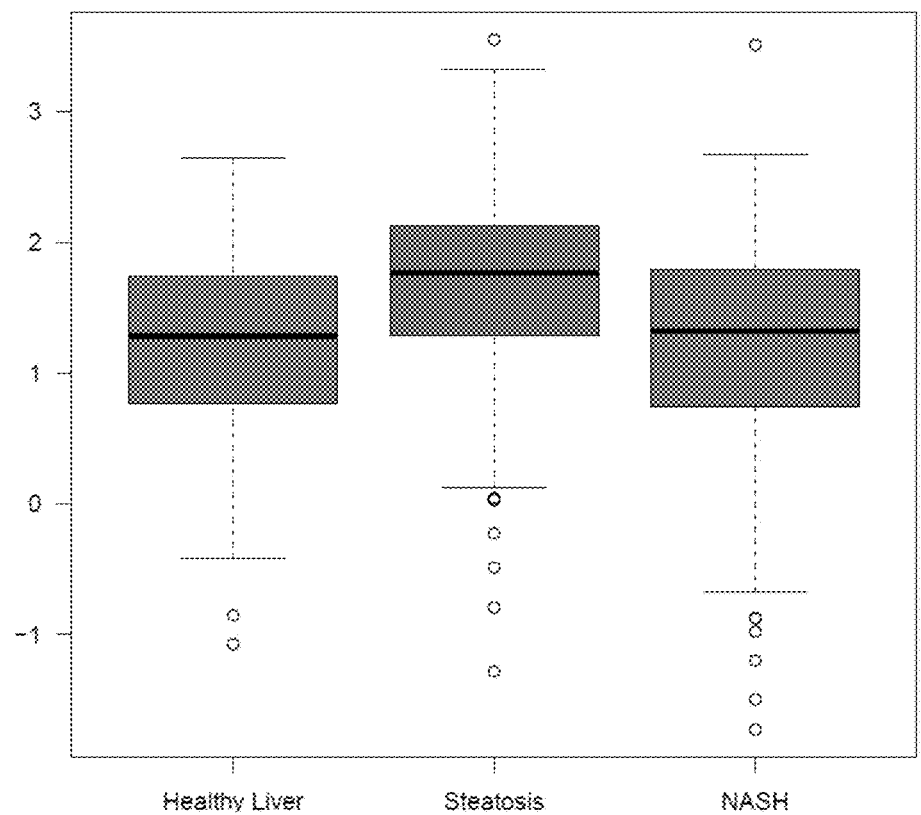
Figure 2T:
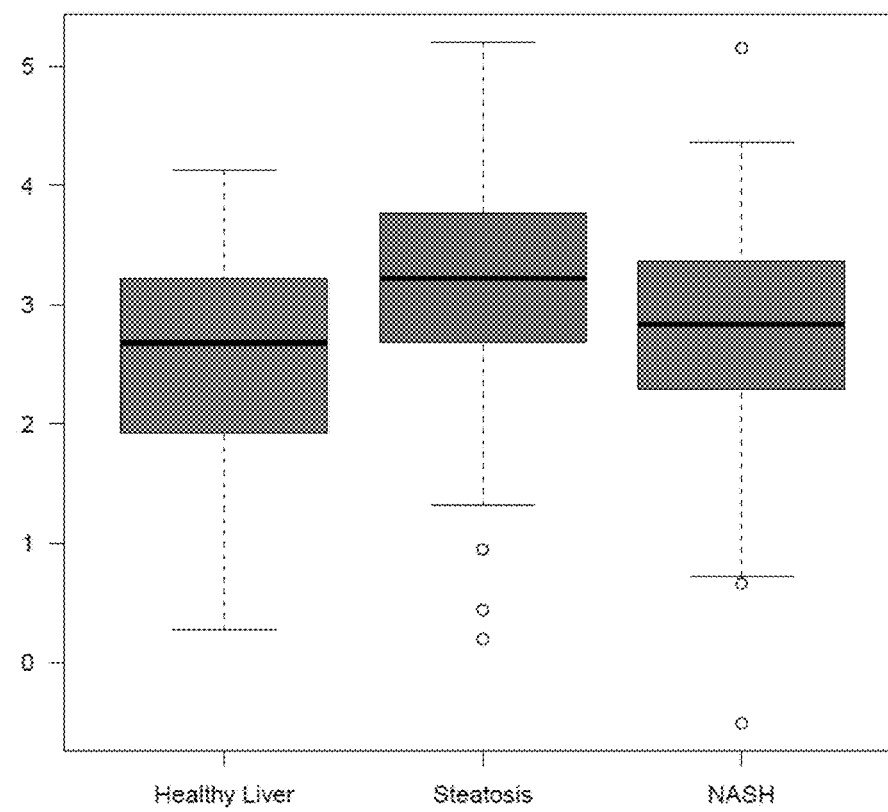

The authors of the present invention have found that there are lipids the levels of which are different in subjects suffering from NAFLD when compared to their levels in healthy subjects (see Example and FIG. 1). Similarly the authors have identified some metabolic markers with differential levels in NASH vs. steatosis (See Example and FIG. 2). The inventors provide herewith non-invasive diagnostic methods based on the determination of levels of said metabolic markers.

DEFINITIONS

The term "body mass index" or "BMI", as used herein, relates to a value derived from the mass (weight) and height of an individual, and defined as the body mass divided by the square of the body height. It is expressed in units of $kg/m^2$, resulting from mass in kilograms and height in metres.

The term "diagnosis", as used herein, refers both to the process of attempting to determine and/or identify a possible disease in a subject, i.e. the diagnostic procedure, and to the opinion reached by this process, i.e. the diagnostic opinion. As such, it can also be regarded as an attempt at classification of an individual's condition into separate and distinct categories that allow medical decisions about treatment and prognosis to be made. It is to be understood that the method, in a preferred embodiment, is a method carried out in vitro, i.e. not practiced on the human or animal body. In particular, the term "diagnosis of a non-alcoholic fatty liver disease (NAFLD)" relates to the capacity to identify or detect the presence of NAFLD in a subject. In a particular embodiment, this term also relates to the capacity to identify or detect the presence of a certain degree of NAFLD progression or stage. In particular, the term "diagnosis of steatosis" relates to the capacity to identify or detect the presence of steatosis in a subject. In a particular embodiment, this term also relates to the capacity to identify or detect the presence of a certain degree of steatosis progression or stage. In particular, the term "diagnosis of NASH" relates to the capacity to identify or detect the presence of NASH in a subject. In a particular embodiment, this term also relates to the capacity to identify or detect the presence of a certain degree of NASH progression or stage. This diagnosis, as it is understood by a person skilled in the art, does not claim to be correct in 100% of the analyzed samples. However, it requires that a statistically significant amount of the analyzed samples are classified correctly. The amount that is statistically significant can be established by a person skilled in the art by means of using different statistical tools; illustrative, non-limiting examples of said statistical tools include determining confidence intervals, determining the p-value, the Student's t-test or Fisher's discriminant functions, etc. The confidence intervals are preferably at least 90%, at least 95%, at least 97%, at least 98% or at least 99%. The p-value is preferably less than 0.1, less than 0.05, less than 0.01, less than 0.005 or less than 0.0001. The teachings of the present invention preferably allow correctly diagnosing in at least 60%, in at least 70%, in at least 80%, or in at least 90% of the subjects of a determined group or population analyzed.

The term "level", as used herein, refers to the quantity of a biomarker detectable in a sample.

The term "logistic regression model" used herein, also known as "logistic regression", "logit regression" or "logit model", relates to a regression model where the dependent variable is categorical. Logistic regression measures the relationship between the categorical dependent variable and one or more independent variables by estimating probabilities using a logistic function, which is the cumulative logistic distribution.

The term "mass spectrometry", as used herein, relates to an analytical technique to identify unknown compounds including: (1) ionizing the compounds and potentially fractionating the compounds parent ion formed into daughter ions; and (2) detecting the charged compounds and calculating a mass-to-charge ratio (m/z). The compounds may be ionized and detected by any suitable means. A "mass spectrometer" includes means for ionizing compounds and for detecting charged compounds.

The term "metabolic marker", as used herein, refers to small molecule compounds, such as substrates for enzymes of metabolic pathways, intermediates of such pathways or the products obtained by a metabolic pathway, the occurrence or amount of which is characteristic for a specific situation, for example NAFLD. The metabolic markers useful for the first diagnostic method of the invention are those defined in Table 1, and for the second diagnostic method of the invention are those defined in Table 3. As shown in Table 1 and Table 3, the metabolic markers could be a single lipid specie or a mixture of various isomers that share the same mass-to-charge ratio (m/z) and retention time (RT). The abbreviated names of the lipid metabolites correspond to the lipid family to which it belongs followed by its lipid number. The lipid family is further described by the reference number of said lipid family in the LIPID MAPS structure database (http://www.lipidmaps.org/data/database-s.html) using the LIPID MAPS Classification System (Fahy E. et al., Journal of Lipid Research 2009, 50: S9-S14). The "lipid number", as the skilled person knows, is a number with the format N:n, where "N" corresponds to the number of carbons in the fatty acid chains and "n" corresponds to the number of double bonds in the fatty acid chains. The lipid metabolic markers of table 1 and table 3 are intended to refer to any isomer thereof, including structural and geometric isomers. The term "structural isomer", as used herein, refers to any of two or more chemical compounds, having the same molecular formula but different structural formulas. The term "geometric isomer" or "stereoisomer" as used herein refers to two or more compounds which contain the same number and types of atoms, and bonds (i.e., the connectivity between atoms is the same), but which have different spatial arrangements of the atoms, for example cis and trans isomers of a double bond, enantiomers, and diastereomers.

The term "non-alcoholic fatty liver disease" or "NAFLD", as used herein, refers to a group of conditions having in common the accumulation of fat in the hepatocytes, NAFLD ranges from simple fatty liver (steatosis), to nonalcoholic steatohepatitis (NASH), to cirrhosis (irreversible, advanced scarring of the liver). The term "NAFLD" includes any stage or degree of progression of the disease.

The term "non-alcoholic steatohepatitis" or "NASH", as used herein, relates to a significant form of chronic liver disease characterized by inflammatory and fatty infiltration of the liver that is not associated with alcohol consumption.

The term "score", as used herein, and also known as predictive factor, relates to the numerical result of a test, and it is an estimate of the likelihood of the condition of a patient condition.

The term "reference value", as used herein, relates to a predetermined criteria used as a reference for evaluating the values or data obtained from the samples collected from a subject. The reference value or reference level can be an absolute value, a relative value, a value that has an upper or a lower limit, a range of values, an average value, a median value, a mean value, or a value as compared to a particular control or baseline value. A reference value can be based on an individual sample value or can be based on a large number of samples, such as from population of subjects of the chronological age matched group, or based on a pool of samples including or excluding the sample to be tested.

The term "sample", as used herein refers to biological material isolated from a subject and therefore includes biological samples. Said sample can contain any biological material suitable for detecting the desired marker and can comprise cells and/or non-cellular material from the subject. In general, a sample can be isolated from any suitable biological tissue or fluid. Particular samples according to the invention include, without limitation, of blood, plasma, serum, saliva, urine and cerebrospinal fluid (CSF). In a particular embodiment of the invention, the sample is selected from blood, serum or plasma. In a preferred embodiment of the invention, the sample is a plasma sample.

The terms "subject", "patient" or "individual"' are used herein interchangeably to refer to all the animals classified as mammals and include but are not limited to domestic and farm animals, primates and humans, for example, human beings, non-human primates, cows, horses, pigs, sheep, goats, dogs, cats, or rodents. Preferably, the subject is a male or female human being of any age or race.

The term "steatosis", as used herein, also known as fatty change, fatty degeneration or adipose degeneration, relates to the process describing the abnormal retention of lipids within a cell.

NAFLD Diagnostic Method (First Diagnostic Method of the Invention)

The inventors have identified a number of lipid serum metabolites the expression of which is increased in those subjects suffering from NAFLD when compared to the expression in healthy subjects (see Table 5 and FIG. 1 in Example section). Therefore, diagnosis of NAFLD can be performed based on determination of the levels of the metabolic markers identified by the inventors following a logistic regression model.

Thus, in a first aspect, the invention relates to an in vitro method for the diagnosis of non-alcoholic fatty liver disease (NAFLD) in a subject that comprises (i) Determining the levels of one or more metabolic markers according to Table 1 in a sample from the subject, and
(ii) Comparing the levels obtained in (i) to a reference value,
wherein the subject is diagnosed with NAFLD according to a score that is obtained by introducing the values of said metabolic marker(s) in a logistic regression model.

In the context of the present invention, the diagnosis of NAFLD according to the first method of the invention relates to the capacity to identify or detect the presence of NAFLD in a subject. This diagnosis, as it is understood by a person skilled in the art, does not claim to be correct in 100% of the analyzed samples. However, it requires that a statistically significant amount of the analyzed samples are classified correctly. The amount that is statistically significant can be established by a person skilled in the art by means of using different statistical tools; illustrative, non-limiting examples of said statistical tools include determining confidence intervals, determining the p-value, the Student's t-test or Fisher's discriminant functions, etc. The confidence intervals are preferably at least 90%, at least 95%, at least 97%, at least 98% or at least 99%. The p-value is preferably less than 0.1, less than 0.05, less than 0.01, less than 0.005 or less than 0.0001. The teachings of the present invention preferably allow correctly diagnosing in at least 60%, in at least 70%, in at least 80%, or in at least 90% of the subjects of a determined group or population analyzed.

In a first step of the first method of the invention, the levels of one or more metabolic markers according to Table 1 are determined in a sample from a subject whose NAFLD diagnosis is to be determined. In a particular embodiment, one metabolic marker according to Table 1 is determined. In a more particular embodiment, at least two, at least three, at least four, at least five, at least six, at least seven, at least eight, at least nine, at least ten, or at least eleven metabolic markers according to Table 1 are determined. In a particular embodiment, the levels of at least 10%, at least 20%, at least 30%, of at least 40%, at least 50%, at least 60%, of at least 70%, at least 80%, or at least 90% of metabolic markers according to Table 1 are determined in a sample from a subject whose NAFLD diagnosis is to be determined. In a more particular embodiment, the levels of all metabolic markers according to Table 1 are determined in a sample from a subject whose NAFLD diagnosis is to be determined.

TABLE 1

Serum lipid metabolites showing differential expression in NAFLD samples versus healthy liver samples. Family name for all of them is triacylglycerols [GL0301] (LIPID MAPS Reference).

| Abbreviated name | Analytes |
|---|---|
| TG(44:1) | TG(14:0 + 18:1 + 12:0) + TG(16:0 + 16:1 + 12:0) |
| TG(46:0) | TG(16:0 + 16:0 + 14:0) |
| TG(48:0) | TG(16:0/16:0/16:0) |
| TG(48:1) | TG(14:0 + 18:1 + 16:0) + TG(16:0 + 16:1 + 16:0) |
| TG(49:1) | TG(15:0 + 18:1 + 16:0) |
| TG(50:2) | TG(16:0 + 18:1 + 16:1) + TG(18:1 + 18:1 + 14:0) + TG(16:0 + 18:2 + 16:0) |
| TG(52:1) | TG(16:0 + 18:1 + 18:0) |
| TG(53:0) | TG(17:0 + 18:0 + 18:0) + TG(20:0 + 17:0 + 16:0) |
| TG(53:1) | TG(18:0 + 18:1 + 17:0) |
| TG(54:5) | TG(18:1 + 20:4 + 16:0) |
| TG(58:2) | TG(18:1 + 22:0 + 18:1) |

"Abbreviated name" corresponds to the addition of the number of carbon atoms and double bonds of the corresponding triglycerides, all of them with the same mass-to-charge ratio (m/z) and retention time (RT). In the "Analytes" column, triglycerides (TG) wherein fatty acid chains are separated by "/" correspond to those TG wherein fatty acid chain positions have been fully identified by the inventors. Triglycerides (TG) wherein fatty acid chains are separated by "+" correspond to TG with the indicated fatty acid chains, in any order.

It will be understood that the biological sample can be analyzed as such or, alternatively, the metabolites may be first extracted from the sample prior to analysis and then the metabolite extract is analyzed. If the metabolites are extracted prior to analysis, different extraction methods are available to the skilled person. The selection of one or other extraction method will depend on the class of metabolites/small molecules that are targeted from a particular analysis. Suitable extraction methods include "Extraction of free metabolite pools", "Vapor Phase Extraction", and "Total Metabolite Extraction". The first type of extraction, "Extraction of free metabolite pools", is mainly used in metabolomics research. In this case free intracellular metabolite pools are obtained from a biological sample through methanol-water extraction for polar metabolites, or chloroform, methanol, chloroform/methanol extraction for non-polar metabolites. The second type of extraction, "Vapor Phase Extraction", refers to the extraction of metabolites that are volatile at room temperature. The metabolites are expelled from the biological sample in the vapor phase. These metabolites are either measured directly by connecting the flask or reactor in which the vapors are generated to the analytical instrument or by absorbing first the vapors in charcoal/solvent and then analyzing the acquired solution. The third type of extraction, "Total Metabolite Extraction", refers to the extraction of the free metabolite pools along with the metabolites that have been incorporated in cellular macromolecules, e.g. lipids, proteins etc. The present invention provides extraction of a particular class of metabolites from macromolecules (e.g. amino acids from proteins or sugars from cell wall components). The present invention also provides a combined high-throughput method which extracts all metabolites simultaneously.

Alternatively, the metabolite quantification can be carried out directly in the biological sample. In this case, the sample may be prepared to enhance detectability of the markers. For example, to increase the detectability of markers, a blood serum sample from the subject can be preferably fractionated by, e.g., Cibacron blue agarose chromatography and single stranded DNA affinity chromatography, anion exchange chromatography, affinity chromatography (e.g., with antibodies) and the like. The method of fractionation depends on the type of detection method used. Any method that enriches for the metabolite of interest can be used. Typically, preparation involves fractionation of the sample and collection of fractions determined to contain the biomarkers. Methods of pre-fractionation include, for example, size exclusion chromatography, ion exchange chromatography, heparin chromatography, affinity chromatography, sequential extraction, gel electrophoresis and liquid chromatography. The analytes also may be modified prior to detection. These methods are useful to simplify the sample for further analysis. For example, it can be useful to remove high abundance proteins, such as albumin, from blood before analysis.

In yet another embodiment, a sample can be pre-fractionated by removing proteins that are present in a high quantity or that may interfere with the detection of markers in a sample. Proteins in general may be removed by using conventional techniques such as precipitation using organic solvents such as methanol precipitation, ethanol, acetonitrile, acetone or combinations thereof, in particular, combination of methanol, acetone and acetonitrile, acid precipitation using, for example, trichloroacetic acid or perchloric acid, heat denaturation and any combination of organic solvent, acid and heat precipitation. In the case of a blood, plasma or serum sample, serum albumin or other proteins abundant in serum such as apolipoproteins, glycoproteins, immunoglobulins may obscure the analysis of markers since they are present in a high quantity. Thus, it may be sufficient to remove one or more of the above proteins albumin in order to detect the metabolites or minor proteins. For this purpose, the blood serum or plasma sample can be pre-fractionated by removing serum albumin. Serum albumin can be removed using a substrate that comprises adsorbents that specifically bind serum albumin. For example, a column which comprises, e.g., Cibacron blue agarose (which has a high affinity for serum albumin) or anti-serum albumin antibodies can be used. In yet another embodiment, a sample can be pre-fractionated by isolating proteins that have a specific characteristic, e.g. are glycosylated. For example, a blood serum or plasma sample can be fractionated by passing the sample over a lectin chromatography column (which has a high affinity for sugars). Many types of affinity adsorbents exist which are suitable for pre-fractionating blood serum or plasma samples. An example of one other type of affinity chromatography available to pre-fractionate a sample is a single stranded DNA spin column. These columns bind proteins which are basic or positively charged. Bound proteins are then eluted from the column using eluants containing denaturants or high pH. Thus there are many ways to reduce the complexity of a sample based on the binding properties of the proteins in the sample, or the characteristics of the proteins in the sample.

In yet another embodiment, a sample can be fractionated using a sequential extraction protocol. In sequential extraction, a sample is exposed to a series of adsorbents to extract different types of bio molecules from a sample.

In a particular embodiment, the determination of the level of one or more metabolic markers is carried out by mass spectrometry. Preferably, mass spectrometry is used in particular gas chromatography coupled to mass spectrometry (GC-MS), liquid chromatography coupled to mass spectrometry (LC-MS), direct infusion mass spectrometry or Fourier transform ion-cyclotrone-resonance mass spectrometry (FT-ICR-MS), capillary electrophoresis coupled to mass spectrometry (CE-MS), high-performance liquid chromatography coupled to mass spectrometry (HPLC-MS), ultra high-performance liquid chromatography coupled to mass spectrometry (UHPLC-MS), supercritical fluid chromatography coupled to mass spectroscopy (SFC-MS), flow injection analysis with mass spectrometry (FIA-MS), including quadrupole mass spectrometry, any sequentially coupled mass spectrometry, such as MS-MS or MS-MS-MS, inductively coupled plasma mass spectrometry (ICP-MS), pyrolysis mass spectrometry (Py-MS), ion mobility mass spectrometry or time-of-flight mass spectrometry (TOF), of electrospray ionization mass spectrometry (ESI-MS), ESI-MS/MS, matrix-assisted laser desorption ionization time-of-flight mass spectrometry (MALDI-TOF-MS), surface-enhanced laser desorption/ionization time-of-flight mass spectrometry (SELDI-TOF MS), desorption/ionization on silicon (DIOS), secondary ion mass spectrometry (SIMS), quadrupole time-of-flight (Q-TOF), atmospheric pressure chemical ionization mass spectrometry (APCI-MS), APCI-MS/MS, APCI-(MS)$^n$, atmospheric pressure photoionization mass spectrometry (APPI-MS), APPI-MS/MS, and APPI-(MS)$^n$, quadrupole mass spectrometry, Fourier transform mass spectrometry (FTMS), and ion trap mass spectrometry, where n is an integer greater than zero. Most preferably, LC-MS is used as described in detail below. Said techniques are disclosed in, e.g., Nissen, Journal of Chromatography A, 703, 1995: 37-57, U.S. Pat. Nos. 4,540,884 or 5,397,894.

The above mentioned ionization methods generally produce an ion resulting from the addition of one or more atoms or by cleavage of the molecule. These ions can then be used as surrogate markers for the metabolites used in the method of the invention. The term "surrogate marker" as used herein means a biological or clinical parameter that is measured in place of the biologically definitive or clinically most meaningful parameter.

Typically, the ions result from the addition of a proton or a hydrogen nucleus, [M+H]<+> where M signifies the molecule of interest, and H signifies the hydrogen ion, which is the same as a proton. Some ionization methods will also produce analogous ions. Analogous ions may arise by the addition of an alkaline metal cation, rather than the proton discussed above. A typical species might be [M+Na]<+>, [M+NH4]<+> or [M+K]<+>. The analysis of the ionized molecules is similar irrespective of whether one is concerned with a protonated ion as discussed above or dealing with an added alkaline metal cation. The major difference is that the addition of a proton adds one mass unit (typically called one Dalton), in case of the hydrogen ion (i.e., proton), 23 Daltons in case of sodium, 18 Daltons in the case of ammonia or 39 Daltons in case of potassium. These additional weights or masses are simply added to the molecular weight of the molecule of interest and the MS peak occurs at the point for the molecular weight of the molecule of interest plus the weight of the ion that has been added. These ionization methods can also produce negative ions. The most common molecular signal is the deprotonated molecule [M–H]<–>, in this case the mass is one Dalton lower than the molecular weight of the molecule of interest. In addition, for some compounds it will be produced multiply charged ions. These are of the general identification type of [M+nH]<n+>, where small n identifies the number of additional protons that have been added.

Preferably, the sample (or the eluent when the sample has been fractionated prior to the mass spectrometry) may be introduced into a high resolution mass spectrometer (for example, a LCT Premier™, Waters Corp., Milford, USA) by electrospray ionization, with capillary and cone voltages set in the positive and negative ion modes to 3200 V and 30 V, and 2800 V and 50 V, respectively. An appropriate test mixture of standard compounds may be analyzed before and after the entire set of randomized injection in order to examine the retention time stability, mass accuracy and sensitivity of the system throughout the course of the run.

In another particular embodiment, the biological sample is fractionated by liquid chromatography prior to the determination of the level(s) of the metabolic marker(s). The term "chromatography", as used herein, refers to a method for mixture component separation that relies on differences in the flowing behavior of the various components of a mixture/solution carried by a mobile phase through a support/column coated with a certain stationary phase. Specifically, some components bind strongly to the stationary phase and spend longer time in the support, while other components stay predominantly in the mobile phase and pass faster through the support. The criterion based on which the various compounds are separated through the column is defined by the particular problem being investigated and imposed by the structure, composition and binding capacity of the stationary phase. For example, a stationary phase could be constructed such that the linear and low molecular weight molecules elute faster than the aromatic and high-molecular weight ones. As the components elute from the support, they can be immediately analyzed by a detector or collected for further analysis. A vast number of separation methods, and in particular chromatography methods, are currently available, including Gas Chromatography (GC), Liquid Chromatography (LC), Ion Chromatography (IC), Size-Exclusion Chromatography (SEC), Supercritical-Fluid Chromatography (SFC), Thin-Layer Chromatography (TLC), High Performance Liquid Chromatography (HPLC), Ultra High Performance Liquid Chromatography (UHPLC), and Capillary Electrophoresis (CE). GC can be used to separate volatile compounds or derivatized compounds that, otherwise, are non-volatile compounds. LC is an alternative chromatographic technique useful for separating ions or molecules that are dissolved in a solvent. The principle of GC and LC separation is the same, their main difference lies on the phase in which the separation occurs (gas vs. liquid phase). In addition, GC is used primarily to separate molecules up to 650 atomic units heavy, while, in principle, a LC can separate any molecular weight compounds. Suitable types of liquid chromatography that can be applied in the method of the invention include, without limitation, reverse phase chromatography, normal phase chromatography, affinity chromatography, ion exchange chromatography, hydrophilic interaction liquid chromatography (HILIC), size exclusion chromatography and chiral chromatography. These techniques are well known in the art and can be applied by the person skilled in the art without further ado.

Once the sample has been processed, the first diagnostic method of the invention involves the determination of the levels of the metabolites according to Table 1 in the sample. The expression "determining the levels of a metabolite", as used herein, refers to ascertaining the absolute or relative amount or concentration of the metabolite in the sample. There are many ways to collect quantitative or relational data on metabolites, and the analytical methodology does not affect the utility of metabolite concentrations in predicting phenotype or assessing metabolism. Suitable methods for determining the levels of a given metabolite include, without limitation, refractive index spectroscopy (RI), Ultra-Violet spectroscopy (UV), fluorescent analysis, radiochemical analysis, Infrared spectroscopy (IR), Nuclear Magnetic Resonance spectroscopy (NMR), Light Scattering analysis (LS), Mass Spectrometry, Pyrolysis Mass Spectrometry, Nephelometry, Dispersive Raman Spectroscopy, gas chromatography combined with mass spectroscopy, liquid chromatography combined with mass spectroscopy, supercritical fluid chromatography combined with mass spectroscopy, MALDI combined with mass spectroscopy, ion spray spectroscopy combined with mass spectroscopy, capillary electrophoresis combined with mass spectrometry, NMR combined with mass spectrometry and IR combined with mass spectrometry.

In a particular embodiment, the levels of the metabolic markers are determined by mass spectrometry. In still more particular embodiment, the biological sample is fractionated by liquid chromatography prior to the determination of the levels of the metabolic markers.

In one still more particular embodiment, the liquid chromatography is performed on a C18 column at 60° C. The column is eluted with a 17 min linear gradient of solvents A (water, acetonitrile and 10 mM ammonium formate), and B (acetonitrile, isopropanol and 10 mM ammonium formate). The mobile phase, at a flow rate of 400 µL/min, initially consisted of 40% solvent B, increasing up to 100% at 10 minutes. After 5 minutes the mobile phase is reset to the initial composition in readiness for the subsequent injection which preceded a 45 s system recycle time.

In a second step of the first method of the invention, the levels of metabolic markers according to Table 1 that are determined in a sample from a subject whose NAFLD diagnosis is to be determined according to step (i) of the method are compared to a reference value. The subject is diagnosed with NAFLD according to a predictive factor or score that is obtained by introducing the values of metabolic marker(s) according to Table 1 in a logistic regression model.

Thus, the first diagnostic method of the invention comprises comparing the level(s) of the metabolic marker(s) according to Table 1 to a reference value.

In a particular embodiment of the first diagnostic method of the invention, the reference value is determined in a sample obtained from one or more healthy subjects, or in a sample from one or more subjects not suffering from NAFLD.

In a particular embodiment of the first diagnostic method of the invention, the application of a predictive factor or score obtained by introducing the values of at least one metabolic marker according to Table 1 in a logistic regression model bases on formula (I):

$$NAFLD(\text{score}) = \frac{1}{1 + e^{-z}} \qquad (I)$$

wherein $$Z = \Sigma_i c_i [A_i^1][A_i^2]$$

$c_i$ is the coefficient estimated for the model for the parameter i, wherein each row represented in the Table 2 is one parameter of the model and $[A_i^1]$ and $[A_i^2]$ are the metabolic marker values. These metabolic marker values are introduced as relative values to the reference value.

In a more particular embodiment of the first diagnostic method of the invention, the application of a predictive factor or score obtained by introducing the values of at least one metabolic marker according to Table 1 and the value of the body mass index (BMI) (kg/m$^2$) in a logistic regression model bases on formula (I) above.

In a particular embodiment, the application of predictive factor or score obtained by introducing the values of at least 10%, at least 20%, at least 30%, of at least 40%, at least 50%, at least 60%, of at least 70%, at least 80%, or at least 90% of metabolic markers according to Table 1 in a logistic regression model bases on formula (I) above.

In a particular embodiment, the application of predictive factor or score obtained by introducing the values of at least 10%, at least 20%, at least 30%, of at least 40%, at least 50%, at least 60%, of at least 70%, at least 80%, or at least 90% of metabolic markers according to Table 1 and the BMI value in a logistic regression model bases on formula (I) above.

In a more particular embodiment, the application of a predictive factor or score obtained by introducing the values of all metabolic markers according to Table 1 in a logistic regression model bases on formula (I) above. In an even more particular embodiment, the application of a predictive factor or score obtained by introducing the values of all metabolic markers according to Table 1 and BMI value in a logistic regression model bases on formula (I) above.

TABLE 2

Parameters of the logistic regression model for the in vitro method for the diagnosis of non-alcoholic fatty liver disease (NAFLD).

| Metabolic Marker Values | | Coefficient |
| --- | --- | --- |
| TG(46:0) | TG(48:0) | 0.0001298 |
| log(TG(49:1)) | TG(53:0) | 0.0137738 |
| TG(50:2) | log(TG(48:1)) | 0.0089746 |
| TG(52:1) | TG(53:1) | 0.0028735 |
| log(TG(54:5)) | log(BMI) | 0.0332303 |
| log(TG(54:5)) | log(TG(52:1)) | 0.0325098 |
| log(TG(58:2)) | log(TG(44:1)) | 0.0399737 |

In a particular embodiment, the subject is diagnosed with NAFLD if NAFLD(score)≥0.5 following formula (I) above. If the score is <0.5, then the subjects is not diagnosed with NAFLD.

NASH/Steatosis Diagnostic Method (Second Diagnostic Method of the Invention)

The inventors have identified metabolic markers the expression of which varies between NAFLD subjects suffering from NASH and NAFLD subjects suffering from steatosis. Thus, a differential diagnosis of NASH or steatosis can be performed for a subject suffering from NAFLD based on the metabolic markers identified by the inventors and shown in Table 3.

Thus, in a second aspect, the invention relates to an in vitro method for the diagnosis of non-alcoholic steatohepatitis (NASH) or steatosis in a subject suffering from NAFLD that comprises
  (i) Determining the levels of one or more metabolic markers according to Table 3 in a sample from the subject, and
  (ii) Comparing the levels obtained in (i) to a reference value,
  wherein the subject is diagnosed of NASH or of steatosis according to a predictive factor or score that is obtained when introducing the values of said metabolic marker(s) in a logistic regression model.

In a particular embodiment, the subject suffering from NAFLD whose diagnosis is intended by the second diagnostic method of the invention is a subject who has been previously diagnosed with NAFLD by the first diagnostic method of the invention.

In the context of the present invention, the diagnosis of NASH or steatosis according to the second method of the invention relates to the capacity to identify or detect the presence of NASH or of steatosis in a subject. This diagnosis, as it is understood by a person skilled in the art, does not claim to be correct in 100% of the analyzed samples. However, it requires that a statistically significant amount of the analyzed samples are classified correctly. The amount that is statistically significant can be established by a person skilled in the art by means of using different statistical tools; illustrative, non-limiting examples of said statistical tools include determining confidence intervals, determining the p-value, the Student's t-test or Fisher's discriminant functions, etc. The confidence intervals are preferably at least 90%, at least 95%, at least 97%, at least 98% or at least 99%. The p-value is preferably less than 0.1, less than 0.05, less than 0.01, less than 0.005 or less than 0.0001. The teachings of the present invention preferably allow correctly diagnosing in at least 60%, in at least 70%, in at least 80%, or in at least 90% of the subjects of a determined group or population analyzed.

In a first step of the second method of the invention, the levels of one or more metabolic markers according to Table 3 are determined in a sample from a subject suffering from NAFLD whose NASH or steatosis diagnosis is to be determined. In a particular embodiment, one metabolic marker according to Table 3 is determined. In a more particular embodiment, at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, at least twenty metabolic markers according to Table 3 are determined. In a particular embodiment, the levels of at least 10%, at least 20%, at least 30%, of at least 40%, at least 50%, at least 60%, of at least 70%, at least 80%, or at least 90% of metabolic markers according to Table 3 are determined in a sample from a subject suffering from NAFLD whose NASH or steatosis diagnosis is to be determined. In a more particular embodiment, the levels of all metabolic markers according to Table 3 are determined in a sample from a subject suffering from NAFLD whose NASH or steatosis diagnosis is to be determined.

TABLE 3

Serum lipid metabolites decreased in NASH samples versus steatosis samples. Family name for all of them is triacylglycerols [GL0301] (LIPID MAPS Reference).

| Abbreviated name | Analytes |
| --- | --- |
| TG(44:1) | TG(14:0 + 18:1 + 12:0) + TG(16:0 + 16:1 + 12:0) |
| TG(48:2) | TG(14:0 + 18:1 + 16:1) + TG(16:0 + 18:2 + 14:0) |
| TG(49:1) | TG(15:0 + 18:1 + 16:0) |
| TG(50:1) | TG(16:0 + 18:1 + 16:0) |
| TG(50:2) | TG(16:0 + 18:1 + 16:1) + TG(18:1 + 18:1 + 14:0) + TG(16:0 + 18:2 + 16:0) |
| TG(51:1) | TG(16:0 + 17:0 + 18:1) |
| TG(51:2) | TG(16:0 + 17:1 + 18:1) |
| TG(51:3) | TG(16:0 + 17:1 + 18:2) + TG(18:2 + 18:1 + 15:0) |
| TG(52:0) | TG(16:0 + 18:0 + 18:0) |
| TG(52:2) | TG(16:0 + 18:1 + 18:1) |
| TG(52:3) | TG(16:0 + 18:1 + 18:2) |
| TG(52:4) | TG(16:0 + 18:2 + 18:2) |
| TG(53:3) | TG(18:2 + 18:1 + 17:0) + TG(18:1 + 18:1 + 17:1) |
| TG(54:2) | TG(18:0 + 18:1 + 18:1) |
| TG(54:3) | TG(20:2 + 20:1 + 14:0) + TG(20:2 + 18:1 + 16:0) + TG(20:1 + 18:2 + 16:0) + TG(18:2 + 18:1 + 18:0) |
| TG(54:5) | TG(18:2 + 18:2 + 18:1) |
| TG(54:6) | TG(20:4 + 18:2 + 16:0) |
| TG(56:3) | TG(18:1 + 20:1 + 18:1) |
| TG(56:7) | TG(22:5 + 18:2 + 16:0) + TG(20:4 + 18:2 + 18:1) |
| TG(56:8) | TG(22:6 + 18:2 + 16:0) |

"Abbreviated name" corresponds to the addition of the number of carbon atoms and double bonds of the corresponding triglycerides, all of them with the same mass-to-charge ratio (m/z) and retention time (RT). In the "Analytes" column, triglycerides (TG) wherein fatty acid chains are separated by "/" correspond to those TG wherein fatty acid chain positions have been fully identified by the inventors. Triglycerides (TG) wherein fatty acid chains are separated by "+" correspond to TG with the indicated fatty acid chains, in any order.

It will be understood that the biological sample can be analyzed as such or, alternatively, the metabolites may be first extracted from the sample prior to analysis and then the metabolite extract is then analyzed, as previously described in the context of the first method of the invention. If the metabolites are extracted prior to analysis, different extraction methods are available to the skilled person. The selection of one or other extraction method will depend on the class of metabolites/small molecules that are targeted from a particular analysis. Suitable extraction methods have been described previously in the context of the first diagnostic method of the invention. Alternatively, the metabolite quantification can be carried out directly in the biological sample, as described previously in the context of the first diagnostic method of the invention. In yet another embodiment, a sample can be pre-fractionated by removing proteins that are present in a high quantity or that may interfere with the detection of markers in a sample, as described previously in the context of the first diagnostic method of the invention.

In a particular embodiment, the determination of the level of one or more metabolic markers is carried out by mass spectrometry. Suitable mass-spectrometry-based techniques and protocols have been described previously in the context of the first diagnostic method of the invention. In another particular embodiment, the biological sample is fractionated by liquid chromatography prior to the determination of the level(s) of the metabolic marker(s), as previously described in the context of the first diagnostic method of the invention.

Once the sample has been processed, the second diagnostic method of the invention involves the determination of the levels of the metabolites according to Table 2 in the sample. Suitable methods for determining the level of a metabolite have been described in the context of the first diagnostic method of the invention. In a particular embodiment, the levels of the metabolic markers are determined by mass spectrometry. In still more particular embodiment, the biological sample is fractionated by liquid chromatography prior to the determination of the levels of the metabolic markers.

In a second step of the second method of the invention, the levels of metabolic markers according to Table 3 that are determined in a sample from a subject whose NASH or steatosis diagnosis is to be determined according to step (i) of the method are compared to a reference value. The subject suffering from NAFLD is diagnosed of NASH or of steatosis according to a predictive factor or score that is obtained when introducing the values of said metabolic marker(s) according to Table 3 in a logistic regression model.

Thus, the second diagnostic method of the invention comprises comparing the level(s) of the metabolic marker(s) according to Table 3 to a reference value.

In a particular embodiment of the second diagnostic method of the invention, the reference value is determined in a sample obtained from one or more healthy subjects, or in a sample from one or more subjects not suffering from NAFLD.

According to the second diagnostic method of the invention, the application of predictive factor or score obtained by introducing the values of at least one metabolic marker according to Table 1 in a logistic regression model bases on formula (II):

$$NASH(\text{score}) = \frac{1}{1+e^{-z}} \quad \text{(II)}$$

wherein $$Z = \sum_i c_i [A_i^1][A_i^2]$$

$c_i$ is the coefficient estimated for the model for the parameter i, wherein each row represented in the Table 4 is one parameter of the model and $[A_i^1]$ and $[A_i^2]$ are the metabolic maker values. These metabolic marker values are introduced as relative values to the reference value.

In a more particular embodiment of the second diagnostic method of the invention, the application of a predictive factor or score obtained by introducing the values of at least one metabolic marker according to Table 3 and the value of the body mass index (BMI) (kg/m$^2$) in a logistic regression model bases on formula (II) above.

In a particular embodiment, the application of predictive factor or score obtained by introducing the values of at least 10%, at least 20%, at least 30%, of at least 40%, at least 50%, at least 60%, of at least 70%, at least 80%, or at least 90% of metabolic markers according to Table 3 in a logistic regression model bases on formula (II) above.

In a more particular embodiment, the application of a predictive factor or score obtained by introducing the values of all metabolic markers according to Table 3 in a logistic regression model bases on formula (II) above. In an even more particular embodiment, the application of a predictive factor or score obtained by introducing the values of all metabolic markers according to Table 3 and BMI value in a logistic regression model bases on formula (II) above.

TABLE 4

Parameters of the logistic regression model for the in vitro method for the diagnosis of non-alcoholic steatohepatitis (NASH) or steatosis in a subject suffering from NAFLD.

| Metabolic Marker Values | | Coefficient |
| --- | --- | --- |
| 1 (*) | 1 (*) | 0.275484780 |
| TG(48:2) | log(TG(50:1)) | −0.073304926 |
| log(TG(51:2)) | log(TG(54.6)) | −0.010113503 |
| log(TG(51:2)) | log(TG(51:3)) | −0.014950028 |
| TG(51:3) | TG(56:3) | 0.007175501 |
| log(TG(52:2)) | log(TG(51:3)) | 0.072283094 |
| log(TG(52:3)) | log(TG(52:2)) | −0.099628336 |
| TG(53:3) | log(TG(56:3)) | −0.030767656 |
| TG(54:2) | log(TG(56:8)) | −0.003197553 |
| TG(54:3) | TG(56:8) | 0.227436782 |
| TG(54:5) | BMI | −0.143003542 |
| TG(54:5) | TG(54:3) | −0.193389015 |
| TG(54:5) | TG(50:1) | 0.097817024 |

(*) First coefficient in the Table 4 is not multiplied by the level value of any of the markers according to Table 3, so a value of 1 is shown in the Table.

In a particular embodiment, the subject suffering from NAFLD is diagnosed with NASH according to the second method of the invention if NASH(score)≥0.5.

In a particular embodiment, the subject suffering from NAFLD is diagnosed with steatosis according to the second method of the invention if NASH(score)<0.5.

In a particular embodiment, the subject suffering from NAFLD has been diagnosed with NAFLD by means of the first method of the invention. Thus, the subject is diagnosed with NASH according to the second method of the invention if:

NAFLD(score)≥0.5 (as previously described in the context of the first method of the invention), and NASH(score)≥0.5, and the subject is diagnosed with steatosis according to the second method of the invention if:

NAFLD(score)≥0.5 (as previously described in the context of the first method of the invention), and NASH(score)<0.5.

The invention is described in detail below by means of the following examples, which are to be construed as merely illustrative and not limitative of the scope of the invention.

EXAMPLES

Materials and Methods

Data of the patients included in the study are the following (values are given as mean±standard deviation of the mean):

N: 467
Ethnicity: Caucasian
Sex (M/F): 24.63% M/75.37% F
Age: 43.8±12.0
BMI (body mass index) (kg/m2): 43.1±11.9
Diagnosis: Healthy liver (90); Steatosis (246); NASH (131)
Biopsy (Yes/No): Yes Sample Preparation Serum was prepared by incubation patient's venous blood in serum separator tubes before centrifugation (2500×g, 15 min); supernatants were aliquoted into microtubes and stored at −80° C. until metabolomic analysis.

Serum samples were divided into aliquots and analyzed in the following metabolomic platform:

Platform—Chloroform/Methanol extract. Proteins were precipitated from the defrosted serum samples (10 µL) by adding 10 µL of sodium chloride (50 mM) and 110 µL of chloroform/methanol (2:1) in 1.5 mL microtubes on ice. The extraction solvent was spiked with TG(13:0/13:0/13:0), not detected in non-spiked human serum extracts. After brief vortex mixing the samples were incubated for 1 h at −20° C. After centrifugation at 16000×g for 15 min, 70 µL of the lower organic phase was collected and the solvent removed. The dried extracts were then reconstituted in 100 µL acetonitrile/isopropanol (50:50), centrifuged (16000×g 5 min), and transferred to vials for UPLC-MS analysis.

Chromatography—Mass Spectrometry Platforms

Chromatography

Chromatography was performed on a 2.1 mm i.d.×100 mm ACQUITY 1.7 µm C18 BEH column (Waters Corp., Milford, MA) using an ACQUITY UPLC system (Waters Corp., Milford, MA). The column was maintained at 60° C. and eluted with a 10 min linear gradient. The mobile phase, at a flow rate of 400 µL/min, initially consisted of 60% solvent A (Water+Acetonitrile+10 mM Ammonium Formate) and 40% solvent B (Acetonitrile+Isopropanol+10 mM Ammonium Formate), increasing to 100% B over 10 minutes. After 5 minutes the mobile phase was reset to the initial composition in readiness for the subsequent injection which proceeded a 45 s system recycle time. The volume of sample injected onto the column was 3 µL.

Mass Spectrometry

The eluent was introduced into the mass spectrometer, Xevo G2 QTof or Synapt G2 QTof (Waters Corp., Milford, MA) by electrospray ionization, with capillary and cone voltages set in the positive ion mode to 3200 and 30 V. The nebulization gas was set to 1000 L/h at a temperature of 500° C. The cone gas was set to 30 L/h, and the source temperature was set to 120° C. Centroid data were acquired from m/z 50-1200 using an accumulation time of 0.2 s per spectrum. All spectra were mass corrected in real time by reference to leucine enkephalin, infused at 10 µL/min through an independent reference electrospray, sampled every 10 s. An appropriate test mixture of standard compounds may be analysed before and after the entire set of randomized sample injections, in order to examine the retention time stability, mass accuracy and sensitivity of the system throughout the course of the run which lasted a maximum of 48 h per batch of samples injected.

Online tandem mass spectrometry (MS/MS) experiments for metabolite identification were performed on an Acquity- Synapt G2-QTof system (Waters Corp., Milford, MA) instrument operating in both the positive and negative ion electrospray modes; source parameters were identical to those employed in the profiling experiments, except for the cone voltage which was increased (30-70 V) when pseudo MS/MS/MS data was required. During retention time windows corresponding to the elution of the compounds under investigation, the quadrupole was set to resolve and transmit ions with appropriate mass-to-charge values. The selected ions then traversed an argon-pressurized cell, with collision energy voltage (typically between 5 and 50 V) applied in accordance with the extent of ion fragmentation required. Subsequent TOF analysis of the fragment ions generated accurate mass generally <3 ppm MS/MS or pseudo MS/MS/MS spectra corrected in real time by reference to leucine enkephalin, infused at 10 µL/min through an independent reference electrospray, sampled every 10 s.

Data Processing

All data were processed using the TarkerLynx application manager for MassLynx 4.1 software (Waters Corp., Milford, MA). The complete set of predefined RT-m/z pairs was fed into the software, which generated associated extracted ion chromatograms (mass tolerance window=0.05 Da), peak-detected and noise-reduced in both the LC and MS domains. A list of intensities (chromatographic peak areas) was then generated for each sample injection, using the RT-m/z pairs (retention time tolerance=6 s) as identifiers. Intra- and interbatch normalization followed the procedure summarized in the paper Martinez-Arranz et al. This process involved (i) internal standard response correction (intrabatch normalization) and (ii) variable specific interbatch single point external calibration using repeat extracts of a commercial serum sample (interbatch normalization).

Statistical Analysis

Multivariate analysis was applied for the creation of predictive models. Briefly, metabolomics data and BMI-continuous were treated with Box-Cox transformation and then a logistic regression model was performed to identify a predictive signature capable of firstly discriminating between healthy liver and NAFLD and secondly between NASH and simple steatosis. A forward stepwise method was used as variable selection criterion, where the analysis started with an empty model and variables were added one at a time as long as these inclusions were worthy. Once a variable was added, the model was evaluated to ensure its discriminatory capability. This process ended when no more variables could be added. Variables with missing values were not included in the analysis as they would provide useless information in this classification method. The inclusion of BMI as a continuous variable in a logistic regression model avoids possible discrepancies in diagnoses when considered the edge cutoff. Receiver operating characteristic (ROC) curve analysis was used to assess the discriminatory power. Overall diagnostic accuracy for a given two-class comparison was done by the area under the ROC curve (AUROC) with its associated standard error. Sensitivity, specificity and positive and negative predictive values were calculated. Once the models were created, they were blind-validated using an independent cohort of patients, different from the one employed to created the first models.

All calculations were performed using R v.2.14.1 (R Development Core Team, 2011) with caret, caTools and receiver operating characteristic R (ROCR) packages to produce ROC curves and AUROC estimate, and MASS package to generate the logistic regression models.

Table 5 shows the specific p-values (Student t-test), fold change, adduct, retention time and mass to charge, for the increased lipid serum metabolites in the NAFLD patients versus healthy liver patients Table 5 showing p-values (Student t-test), fold change, adduct, retention time and mass to charge, for the increased lipid serum metabolites in the NAFLD patients versus healthy liver patients

| Abbreviated name | Analyte | Fold Change NAFLD/Healthy liver | Retention time | Mass to charge | Student t-test (NAFLD) | Adduct |
|---|---|---|---|---|---|---|
| TG(44:1) | TG(14:0 + 18:1 + 12:0) + TG(16:0 + 16:1 + 12:0) | 1.3053 | 7.24 | 766.693 | 0.3140 | [M + NH4]+ |
| TG(46:0) | TG(16:0 + 16:0 + 14:0) | 1.4697 | 7.83 | 796.739 | 0.0319 | [M + NH4]+ |
| TG(48:0) | TG(16:0/16:0/16:0) | 1.7767 | 8.11 | 824.771 | 0.0000 | [M + NH4]+ |
| TG(48:1) | TG(14:0 + 18:1 + 16:0) + TG(16:0 + 16:1 + 16:0) | 1.5418 | 7.83 | 822.755 | 0.0003 | [M + NH4]+ |
| TG(49:1) | TG(15:0 + 18:1 + 16:0) | 1.2778 | 7.95 | 836.771 | 0.0654 | [M + NH4]+ |
| TG(50:2) | TG(16:0 + 18:1 + 16:1) + TG(18:1 + 18:1 + 14:0) + TG(16:0 + 18:2 + 16:0) | 1.4162 | 7.84 | 848.771 | 0.0000 | [M + NH4]+ |
| TG(52:1) | TG(16:0 + 18:1 + 18:0) | 1.6407 | 8.32 | 878.818 | 0.0000 | [M + NH4]+ |
| TG(53:0) | TG(17:0 + 18:0 + 18:0) + TG(20:0 + 17:0 + 16:0) | 1.2525 | 8.66 | 894.849 | 0.0600 | [M + NH4]+ |
| TG(53:1) | TG(18:0 + 18:1 + 17:0) | 1.4580 | 8.43 | 892.833 | 0.0087 | [M + NH4]+ |
| TG(54:5) | TG(18:2 + 18:2 + 18:1) | 1.6592 | 7.58 | 898.786 | 0..000 | [M + NH4]+ |
| TG(58:2) | TG(18:1 + 22:0 + 18:1) | 2.1921 | 8.74 | 960.896 | 0.0000 | [M + NH4]+ |

Table 6 showing the specific p-values (Student t-test), fold change, adduct, retention time and mass to charge, for the decreased lipid serum metabolites in the NASH patients versus steatosis patients.

| Abbreviated | Analyte | Fold Change | Retention time | Mass to charge | Student t-test | Adduct |
|---|---|---|---|---|---|---|
| TG(44:1) | TG(14:0 + 18:1 + 12:0) + TG(16:0 + 16:1 + 12:0) | 0.9868 | 7.24 | 766.693 | 0.9678 | [M + NH4]+ |
| TG(48:2) | TG(14:0 + 18:1 + 16:1) + TG(16:0 + 18:2 + 14:0) | 0.8343 | 7.55 | 820.739 | 0.0334 | [M + NH4]+ |
| TG(49:1) | TG(15:0 + 18:1 + 16:0) | 0.8939 | 7.95 | 836.771 | 0.2835 | [M + NH4]+ |
| TG(50:1) | TG(16:0 + 18:1 + 16:0) | 1.0190 | 8.09 | 850.786 | 0.7519 | [M + NH4]+ |
| TG(50:2) | TG(16:0 + 18:1 + 16:1) + TG(18:1 + 18:1 + 14:0) + TG(16:0 + 18:2 + 16:0) | 0.9399 | 7.84 | 848.771 | 0.2797 | [M + NH4]+ |
| TG(51:1) | TG(16:0 + 17:0 + 18:1) | 0.9138 | 8.20 | 864.802 | 0.3989 | [M + NH4]+ |
| TG(51:2) | TG(16:0 + 17:1 + 18:1) | 0.8587 | 7.95 | 862.786 | 0.0256 | [M + NH4]+ |
| TG(51:3) | TG(16:0 + 17:1 + 18:2) + TG(18:2 + 18:1 + 15:0) | 0.8088 | 7.69 | 860.771 | 0.0023 | [M + NH4]+ |
| TG(52:0) | TG(16:0 + 18:0 + 18:0) | 0.9822 | 8.56 | 880.833 | 0.9289 | [M + NH4]+ |
| TG(52:2) | TG(16:0 + 18:1 + 18:1) | 0.9891 | 8.08 | 876.802 | 0.7498 | [M + NH4]+ |
| TG(52:3) | TG(16:0 + 18:1 + 18:2) | 0.8945 | 7.85 | 874.786 | 0.0076 | [M + NH4]+ |
| TG(52:4) | TG(16:0 + 18:2 + 18:2) | 0.7481 | 7.60 | 872.771 | 0.0000 | [M + NH4]+ |
| TG(53:3) | TG(18:2 + 18:1 + 17:0) + TG(18:1 + 18:1 + 17:1) | 0.7993 | 7.96 | 888.802 | 0.0002 | [M + NH4]+ |
| TG(54:2) | TG(18:0 + 18:1 + 18:1) | 0.9668 | 8.31 | 904.833 | 0.5341 | [M + NH4]+ |
| TG(54:3) | TG(20:2 + 20:1 + 14:0) + TG(20:2 + 18:1 + 16:0) + TG(20:1 + 18:2 + 16:0) + TG(18:2 + 18:1 + 18:0) | 0.9870 | 8.07 | 902.818 | 0.7594 | [M + NH4]+ |
| TG(54:5) | TG(18:2 + 18:2 + 18:1) | 0.5939 | 7.58 | 898.786 | 0.0000 | [M + NH4]+ |
| TG(54:6) | TG(20:4 + 18:2 + 16:0) | 0.7407 | 7.49 | 896.771 | 0.0001 | [M + NH4]+ |
| TG(56:3) | TG(18:1 + 20:1 + 18:1) | 0.9624 | 8.29 | 930.849 | 0.5954 | [M + NH4]+ |
| TG(56:7) | TG(22:5 + 18:2 + 16:0) + TG(20:4 + 18:2 + 18:1) | 0.6977 | 7.46 | 922.786 | 0.0000 | [M + NH4]+ |
| TG(56:8) | TG(22:6 + 18:2 + 16:0) | 0.7064 | 7.35 | 920.771 | 0.0002 | [M + NH4]+ |

The following tables show the parameters of ROC curves according to the first and second methods of the invention.

TABLE 7

Cross-tabulation of observed and predicted classes with associated statistics for the first method of the invention based on parameters of Table 2 and metabolites according to Table 5.

| | |
|---|---|
| Accuracy | 0.863 |
| 95% CI | (0.8284, 0.8928) |
| No Information Rate | 0.8073 |
| P-Value [Acc > NIR] | 0.0009572 |
| Kappa | 0.4532 |
| Mcnemar's Test P-Value | 1.855e−08 |
| Sensitivity | 0.83333 |
| Specificity | 0.91613 |
| Pos Pred Value | 0.79545 |
| Neg Pred Value | 0.86998 |
| Prevalence | 0.19272 |
| Detection Rate | 0.07495 |
| Detection Prevalence | 0.09422 |
| Balanced Accuracy | 0.68251 |

TABLE 8

Cross-tabulation of observed and predicted classes with associated statistics for the second method of the invention based on parameters of Table 4 and metabolites according to Table 6.

| | |
|---|---|
| Accuracy | 0.8302 |
| 95% CI | (0.7885, 0.8667) |
| No Information Rate | 0.7241 |
| P-Value [Acc > NIR] | 9.302e−07 |
| Kappa | 0.6056 |
| Mcnemar's Test P-Value | 0.001778 |
| Sensitivity | 0.8352 |

TABLE 8-continued

Cross-tabulation of observed and predicted classes with associated statistics for the second method of the invention based on parameters of Table 4 and metabolites according to Table 6.

| | |
|---|---|
| Specificity | 0.8173 |
| Pos Pred Value | 0.9231 |
| Neg Pred Value | 0.6538 |
| Prevalence | 0.7241 |
| Detection Rate | 0.6048 |
| Detection Prevalence | 0.6552 |
| Balanced Accuracy | 0.8262 |

The invention claimed is:

1. A method for discriminating between non-alcoholic steatohepatitis (NASH) and steatosis and correspondingly treating a patient diagnosed with non-alcoholic fatty liver disease (NAFLD), the method comprising:
   (i) fractionating by liquid chromatography a sample isolated from the patient;
   (ii) determining by mass spectrometry the levels of one or more metabolic markers selected from the group consisting of:
      (a) metabolic marker TG(44:1) comprising at least one of analytes TG(14:0+18:1+12:0) and TG(16:0+16:1+12:0);
      (b) metabolic marker TG(48:2) comprising at least one of analytes TG(14:0+18:1+16:1) and TG(16:0+18:2+14:0);
      (c) metabolic marker TG(49:1) comprising analyte TG(15:0+18:1+16:0);
      (d) metabolic marker TG(50:2) comprising at least one of analytes TG(16:0+18:1+16:1), TG(18:1+18:1+14:0), and TG(16:0+18:2+16:0);

(e) metabolic marker TG(51:1) comprising analyte TG(16:0+17:0+18:1);
(f) metabolic marker TG(51:2) comprising analyte TG(16:0+17:1+18:1);
(g) metabolic marker TG(51:3) comprising analyte TG(18:2+18:1+15:0);
(h) metabolic marker TG(52:0) comprising analyte TG(16:0+18:0+18:0);
(i) metabolic marker TG(52:3) comprising analyte TG(16:0+18:1+18:2);
(j) metabolic marker TG(52:4) comprising analyte TG(16:0+18:2+18:2);
(k) metabolic marker TG(53:3) comprising at least one of analytes TG(18:2+18:1+17:0) and TG(18:1+18:1+17:1);
(l) metabolic marker TG(54:2) comprising analyte TG(18:0+18:1+18:1);
(m) metabolic marker TG(54:3) comprising at least one of analytes TG(20:2+20:1+14:0), TG(20:2+18:1+16:0), TG(20:1+18:2+16:0), and TG(18:2+18:1+18:0);
(n) metabolic marker TG(54:5) comprising analyte TG(18:2+18:2+18:1);
(o) metabolic marker TG(54: 6) comprising analyte TG(20: 4+18:2+16: 0);
(p) metabolic marker TG(56:3) comprising analyte TG(18:1+20:1+18:1);
(q) metabolic marker TG(56:7) comprising at least one of analytes TG(22:5+18:2+16:0) and TG(20:4+18:2+18:1); and
(r) metabolic marker TG(56:8) comprising analyte TG(22:6+18:2+16:0),
(iii) generating a predictive score based on relative values of the metabolic markers in a logistic regression model to discriminate between NASH and steatosis, wherein the predictive score is given by formula (I)

$$\text{predictive score} = \frac{1}{1+e^{-z}} \quad \text{(I)}$$

wherein $$Z = \sum_i c_i [A_i^1][A_i^2]$$

$c_i$ is the coefficient estimated for the model for the parameter i, wherein each parameter i of the model includes $A_i^1$ and $A_i^2$, wherein $A_i^1$ is a first metabolic marker of (a)-(r) determined in (ii) or a first metabolic marker logarithm, and $A_i^2$ is a second metabolic marker of (a)-(r) determined in (ii), second metabolic marker logarithm, body mass index, or body mass index logarithm and $[A_i^1]$ and $[A_i^2]$ are corresponding relative values of $A_i^1$ and $A_i^2$ based on metabolic marker levels obtained in (ii); and
(iv) treating the patient for NASH when the predictive score is ≥0.5, and treating the patient for steatosis when the predictive score is <0.5.

2. The method according to claim 1, wherein the reference value is determined in a sample from one or more healthy subjects or from one or more subjects not suffering from NAFLD.

3. The method according to claim 1, wherein the levels of all metabolic markers of claim 1 are determined.

4. The method according to claim 1, wherein a body mass index (BMI) value is introduced in the logistic regression model.

5. The method according to claim 1, wherein the subject suffering from NAFLD has been previously diagnosed of NAFLD by an in vitro method that comprises:
(i) determining in a sample from the subject the levels of one or more metabolic markers selected from the group consisting of:
(a) metabolic marker TG(44:1) comprising at least one of analytes TG(14:0+18:1+12:0) and TG(16:0+16:1+12:0);
(b) metabolic marker TG(46:0) comprising analyte TG(16:0+16:0+14:0);
(c) metabolic marker TG(48:0) comprising analyte TG(16:0/16:0/16:0);
(d) metabolic marker TG(48:1) comprising at least one of analytes TG(14:0+18:1+16:0) and TG(16:0+16:1+16:0);
(e) metabolic marker TG(49:1) comprising analyte TG(15:0+18:1+16:0);
(f) metabolic marker TG(50:2) comprising at least one of analytes TG(16:0+18:1+16:1), TG(18:1+18:1+14:0), and TG(16:0+18:2+16:0);
(g) metabolic marker TG(52:1) comprising analyte TG(16:0+18:1+18:0);
(h) metabolic marker TG(53:0) comprising at least one of analytes TG(17:0+18:0+18:0) and TG(20:0+17:0+16:0);
(i) metabolic marker TG(53:1) comprising analyte TG(18:0+18:1+17:0);
(j) metabolic marker TG(54:5) comprising analyte TG(18:1+20:4+16:0); and
(k) metabolic marker TG(58:2) comprising analyte TG(18:1+22:0+18:1), and
(ii) comparing the levels obtained in (i) to a reference value to obtain a relative value, wherein the subject is diagnosed with NAFLD according to a score that is obtained by introducing the relative values of said metabolic marker(s) in a logistic regression model.

6. The method according to claim 1, wherein the sample is a serum sample.

7. A method for discriminating between non-alcoholic steatohepatitis (NASH) and steatosis and correspondingly treating a subject previously diagnosed with non-alcoholic fatty liver disease (NAFLD), the method comprising:
(i) fractionating by liquid chromatography a serum sample isolated from the subject;
(ii) determining by mass spectrometry the levels of one or more metabolic markers selected from the group consisting of:
(a) metabolic marker TG(44:1) comprising at least one of analytes TG(14:0+18:1+12:0) and TG(16:0+16:1+12:0);
(b) metabolic marker TG(48:2) comprising at least one of analytes TG(14:0+18:1+16:1) and TG(16:0+18:2+14:0);
(c) metabolic marker TG(49:1) comprising analyte TG(15:0+18:1+16:0);
(d) metabolic marker TG(50:1) comprising analyte TG(16:0+18:1+16:0);
(e) metabolic marker TG(51:1) comprising analyte TG(16:0+17:0+18:1);
(f) metabolic marker TG(51:2) comprising analyte TG(16:0+17:1+18:1);
(g) metabolic marker TG(51:3) comprising analyte TG(18:2+18:1+15:0);

(h) metabolic marker TG(52:0) comprising analyte TG(16:0+18:0+18:0);
(i) metabolic marker TG(52:3) comprising analyte TG(16:0+18:1+18:2);
(j) metabolic marker TG(52:4) comprising analyte TG(16:0+18:2+18:2);
(k) metabolic marker TG(53:3) comprising at least one of analytes TG(18:2+18:1+17:0) and TG(18:1+18:1+17:1);
(l) metabolic marker TG(54:2) comprising analyte TG(18:0+18:1+18:1);
(m) metabolic marker TG(54:3) comprising at least one of analytes TG(20:2+20:1+14:0), TG(20:2+18:1+16:0), TG(20:1+18:2+16:0), and TG(18:2+18:1+18:0);
(n) metabolic marker TG(54:5) comprising analyte TG(18:2+18:2+18:1);
(o) metabolic marker TG(54:6) comprising analyte TG(20:4+18:2+16:0);
(p) metabolic marker TG(56:3) comprising analyte TG(18:1+20:1+18:1);
(q) metabolic marker TG(56:7) comprising at least one of analytes TG(22:5+18:2+16:0) and TG(20:4+18:2+18:1); and
(r) metabolic marker TG(56:8) comprising analyte TG(22:6+18:2+16:0); and (iii) comparing each of the levels obtained in (ii) to a reference value to obtain a relative value;
(iv) generating a predictive score based on the relative values of the metabolic markers in a logistic regression model to discriminate between NASH and steatosis, wherein the predictive score is given by formula (I)

$$\text{predictive score} = \frac{1}{1+e^{-z}} \quad (I)$$

wherein $$Z = \sum_i c_i [A_i^1][A_i^2]$$

$c_i$ is the coefficient estimated for the model for the parameter i, wherein each parameter i of the model includes $A_i^1$ and $A_i^2$ wherein $A_i^1$ is a first metabolic marker of (a)-(r) determined in (ii) or a first metabolic marker logarithm, and $A_i^2$ is a second metabolic marker of (a)-(r) determined in (ii), second metabolic marker logarithm, body mass index, or body mass index logarithm and $[A_i^1]$ and $[A_i^2]$ are corresponding relative values of $A_i^1$ and $A_i^2$; and (v) treating the patient for NASH when the predictive score is ≥0.5, and treating the patient for steatosis when the predictive score is <0.5.

\* \* \* \* \*